United States Patent
Yamada et al.

(10) Patent No.: US 7,108,987 B2
(45) Date of Patent: Sep. 19, 2006

(54) FACTORS PARTICIPATING IN DEGRANULATION OF MAST CELLS, DNAS ENCODING THE SAME, METHOD OF SCREENING OF THESE FACTORS AND THE INHIBITORS

(75) Inventors: Tsuyoshi Yamada, Kisarazu (JP); Motoharu Ido, Otsu (JP)

(73) Assignee: Dainippon Pharmaceutical Co., Ltd., Osaka (JP)

( * ) Notice: Subject to any disclaimer, the term of this patent is extended or adjusted under 35 U.S.C. 154(b) by 502 days.

(21) Appl. No.: 10/258,107

(22) PCT Filed: Apr. 16, 2001

(86) PCT No.: PCT/JP01/03268

§ 371 (c)(1),
(2), (4) Date: Dec. 19, 2002

(87) PCT Pub. No.: WO01/79478

PCT Pub. Date: Oct. 25, 2001

(65) Prior Publication Data

US 2003/0143633 A1      Jul. 31, 2003

(30) Foreign Application Priority Data

Apr. 19, 2000   (JP) .............................. 2000-118408

(51) Int. Cl.
*G01N 33/53* (2006.01)
*C12Q 1/34* (2006.01)
*C12N 9/14* (2006.01)

(52) U.S. Cl. ........................... 435/7.1; 435/18; 435/195

(58) Field of Classification Search ................ 435/195, 435/7.1, 18

See application file for complete search history.

(56) References Cited

U.S. PATENT DOCUMENTS 5,843,717 A * 12/1998 Hillman et al. ............ 435/69.1

6,391,580 B1 * 5/2002 Hillman et al. ............ 435/69.1

FOREIGN PATENT DOCUMENTS

| WO | WO 87/06127 A1 | 10/1987 |
| WO | WO 99/42586 A3 | 8/1999 |
| WO | WO 00/58464 A3 | 10/2000 |
| WO | WO 01/64887 A2 | 9/2001 |

OTHER PUBLICATIONS

Wagner et al (1995) Biochemical and Biophysicam Res. Communications, vol. 207, pp. 950-956.*
Oberhauser et al. (1994) FEBS Letters, vol. 339, pp. 171-174.*
Masuda et al., "Rab37 is a novel mast cell specific GTPase localized to secretory granules;" *FEBS Letters*, 470 (1), 61-64 (Mar. 17, 2000).
Mizuki et al., "Functional modules and expression of mouse $p40^{phox}$ and $p67^{phox}$, SH3-domain-containing proteins involved in the phagocyte NDAPH oxidase complex," *European Journal of Biochemistry*, 251 (3), 573-582 (1998).
Leto et al., "Cloning of a 67-kD Neutrophil Oxidase Factor with Similarity to a Noncatalytic Region of $p60^{c-src}$," *Science*, 248, 727-730 (1990).
Belik et al., "Correlation between structure and radioprotective activity (RPA) in thiazole derivatives," *Radiats. Biol. Radioecol.*, 33 (6), 824-830 (1993).
Jager et al., "Serological Cloning of a Melanocyte *rab* Guanosine 5'-Triphosphate-binding Protein and a Chromosome Condensation Protein from a Melanoma Complementary DNA Library," *Cancer Research*, 60 (13), 3584-3591 (2000).
Gonzalez et al., *Cell*, 96(6): 755-758 (1999).
Roa et al., *Journal of Immunology*, 159(6): 2815-2823 (1997).

* cited by examiner

*Primary Examiner*—Elizabeth Slobodyansky
(74) *Attorney, Agent, or Firm*—Leydig, Volt & Mayer, Ltd.

(57) ABSTRACT

The present invention provides a novel protein that regulates degranulation of mast cells (degranulation regulator), a gene encoding it, a protein (conjugate factor) that interacts with the regulator, a gene encoding it, a screening method of an inhibitor of the degranulation, which uses this degranulation regulator and the conjugate factor, an inhibitor obtained by the screening method and the like.

7 Claims, No Drawings

SEQUENCE LISTING

<160> NUMBER OF SEQ ID NOS: 20

<210> SEQ ID NO 1
<211> LENGTH: 191
<212> TYPE: PRT
<213> ORGANISM: Mus musculus or Homo sapiens
<220> FEATURE:
<221> NAME/KEY: Misc_feature
<222> LOCATION: (45)
<223> OTHER INFORMATION: Ala or Val.
<220> FEATURE:
<221> NAME/KEY: Misc_feature
<222> LOCATION: (115)
<223> OTHER INFORMATION: Val or Met.
<220> FEATURE:
<221> NAME/KEY: Misc_feature
<222> LOCATION: (138)
<223> OTHER INFORMATION: Met or Leu.
<220> FEATURE:
<221> NAME/KEY: Misc_feature
<222> LOCATION: (165)
<223> OTHER INFORMATION: Arg or His.
<220> FEATURE:
<221> NAME/KEY: Misc_feature
<222> LOCATION: (167)
<223> OTHER INFORMATION: Pro or Ala.

<400> SEQUENCE: 1

Met Leu Leu Gly Asp Ser Gly Val Gly Lys Thr Cys Phe Leu Ile Gln
 1               5                   10                  15

Phe Lys Asp Gly Ala Phe Leu Ser Gly Thr Phe Ile Ala Thr Val Gly
            20                  25                  30

Ile Asp Phe Arg Asn Lys Val Val Thr Val Asp Gly Xaa Arg Val Lys
        35                  40                  45

Leu Gln Ile Trp Asp Thr Ala Gly Gln Glu Arg Phe Arg Ser Val Thr
    50                  55                  60

His Ala Tyr Tyr Arg Asp Ala Gln Ala Leu Leu Leu Leu Tyr Asp Ile
65                  70                  75                  80

Thr Asn Lys Ser Ser Phe Asp Asn Ile Arg Ala Trp Leu Thr Glu Ile
                85                  90                  95

His Glu Tyr Ala Gln Arg Asp Val Val Ile Met Leu Leu Gly Asn Lys
            100                 105                 110

Ala Asp Xaa Ser Ser Glu Arg Val Ile Arg Ser Glu Asp Gly Glu Thr
        115                 120                 125

Leu Ala Arg Glu Tyr Gly Val Pro Phe Xaa Glu Thr Ser Ala Lys Thr
    130                 135                 140

Gly Met Asn Val Glu Leu Ala Phe Leu Ala Ile Ala Lys Glu Leu Lys
145                 150                 155                 160

Tyr Arg Ala Gly Xaa Gln Xaa Asp Glu Pro Ser Phe Gln Ile Arg Asp
                165                 170                 175

Tyr Val Glu Ser Gln Lys Lys Arg Ser Ser Cys Cys Ser Phe Val
            180                 185                 190

<210> SEQ ID NO 2
<211> LENGTH: 576
<212> TYPE: DNA
<213> ORGANISM: Mus musculus

<400> SEQUENCE: 2 atg ctt ctt gga gac tcg ggc gtc ggc aaa acc tgt ttc ctg atc caa    48
Met Leu Leu Gly Asp Ser Gly Val Gly Lys Thr Cys Phe Leu Ile Gln
 1               5                   10                  15

-continued

```
ttc aaa gac ggg gcc ttc ctg tcc gga acc ttc ata gcc acc gtc ggc      96
Phe Lys Asp Gly Ala Phe Leu Ser Gly Thr Phe Ile Ala Thr Val Gly
         20                  25                  30 ata gac ttc agg aat aaa gtg gtg aca gtg gat ggt gcc agg gtg aag     144
Ile Asp Phe Arg Asn Lys Val Val Thr Val Asp Gly Ala Arg Val Lys
 35                  40                  45 ctt cag atc tgg gac act gca gga cag gag cgc ttt cgc agt gtg acc     192
Leu Gln Ile Trp Asp Thr Ala Gly Gln Glu Arg Phe Arg Ser Val Thr
 50                  55                  60 cat gct tat tac cga gat gct cag gct ttg ctc ctg ttg tat gac atc     240
His Ala Tyr Tyr Arg Asp Ala Gln Ala Leu Leu Leu Leu Tyr Asp Ile
 65                  70                  75                  80 acc aac cag tcc tct ttt gac aac atc agg gcc tgg ctc aca gag att     288
Thr Asn Lys Ser Ser Phe Asp Asn Ile Arg Ala Trp Leu Thr Glu Ile
                 85                  90                  95 cat gag tat gcc cag aga gac gtg gtg att atg ctt cta ggc aac aag     336
His Glu Tyr Ala Gln Arg Asp Val Val Ile Met Leu Leu Gly Asn Lys
            100                 105                 110 gcc gat gta agc agc gaa agg gtg atc cgt tct gaa gat gga gag aca     384
Ala Asp Val Ser Ser Glu Arg Val Ile Arg Ser Glu Asp Gly Glu Thr
        115                 120                 125 ctg gcc agg gaa tat ggt gtt cct ttc atg gag acc agt gcc aag act     432
Leu Ala Arg Glu Tyr Gly Val Pro Phe Met Glu Thr Ser Ala Lys Thr
    130                 135                 140 ggc atg aac gtg gag ttg gcc ttt ctg gca att gcc aag gaa ctg aaa     480
Gly Met Asn Val Glu Leu Ala Phe Leu Ala Ile Ala Lys Glu Leu Lys
145                 150                 155                 160 tac cgt gca ggg agg cag cct gat gag ccc agc ttc cag atc cga gac     528
Tyr Arg Ala Gly Arg Gln Pro Asp Glu Pro Ser Phe Gln Ile Arg Asp
                165                 170                 175 tat gtg gag tcc cag aag aag cgc tcc agc tgc tgc tcc ttt gtg tga    576
Tyr Val Glu Ser Gln Lys Lys Arg Ser Ser Cys Cys Ser Phe Val
            180                 185                 190

<210> SEQ ID NO 3
<211> LENGTH: 576
<212> TYPE: DNA
<213> ORGANISM: Homo sapiens

<400> SEQUENCE: 3 atg ctt ctt gga gac tcg ggc gtc ggc aaa aca tgt ttc ctg atc caa      48
Met Leu Leu Gly Asp Ser Gly Val Gly Lys Thr Cys Phe Leu Ile Gln
  1               5                  10                  15 ttc aaa gac ggg gcc ttc ctg tcc gga acc ttc ata gcc acc gtc ggc      96
Phe Lys Asp Gly Ala Phe Leu Ser Gly Thr Phe Ile Ala Thr Val Gly
         20                  25                  30 ata gac ttc agg aac aag gtg gtg act gtg gat ggc gtg aga gtg aag     144
Ile Asp Phe Arg Asn Lys Val Val Thr Val Asp Gly Val Arg Val Lys
 35                  40                  45 ctg cag atc tgg gac acc gct ggg cag gaa cgg ttc cga agc gtc acc     192
Leu Gln Ile Trp Asp Thr Ala Gly Gln Glu Arg Phe Arg Ser Val Thr
 50                  55                  60 cat gct tat tac aga gat gct cag gcc ttg ctt ctg tat gac atc         240
His Ala Tyr Tyr Arg Asp Ala Gln Ala Leu Leu Leu Tyr Asp Ile
 65                  70                  75                  80 acc aac aaa tct tct ttc gac aac atc agg gcc tgg ctc act gag att     288
Thr Asn Lys Ser Ser Phe Asp Asn Ile Arg Ala Trp Leu Thr Glu Ile
                 85                  90                  95 cat gag tat gcc cag agg gac gtg gtg atc atg ctg cta ggc aac aag     336
His Glu Tyr Ala Gln Arg Asp Val Val Ile Met Leu Leu Gly Asn Lys
```

-continued

```
                 100                 105                 110
gcg gat atg agc agc gaa aga gtg atc cgt tcc gaa gac gga gag acc      384
Ala Asp Met Ser Ser Glu Arg Val Ile Arg Ser Glu Asp Gly Glu Thr
        115                 120                 125 ttg gcc agg gag tac ggt gtt ccc ttc ctg gag acc agc gcc aag act      432
Leu Ala Arg Glu Tyr Gly Val Pro Phe Leu Glu Thr Ser Ala Lys Thr
130                 135                 140 ggc atg aat gtg gag tta gcc ttt ctg gcc atc gcc aag gaa ctg aaa      480
Gly Met Asn Val Glu Leu Ala Phe Leu Ala Ile Ala Lys Glu Leu Lys
145                 150                 155                 160 tac cgg gcc ggg cat cag gcg gat gag ccc agc ttc cag atc cga gac      528
Tyr Arg Ala Gly His Gln Ala Asp Glu Pro Ser Phe Gln Ile Arg Asp
                165                 170                 175 tat gta gag tcc cag aag aag cgc tcc agc tgc tgc tcc ttt gtg tga      576
Tyr Val Glu Ser Gln Lys Lys Arg Ser Ser Cys Cys Ser Phe Val
        180                 185                 190
```

<210> SEQ ID NO 4
<211> LENGTH: 211
<212> TYPE: PRT
<213> ORGANISM: Mus musculus or Homo sapiens
<220> FEATURE:
<221> NAME/KEY: Misc_feature
<222> LOCATION: (113)
<223> OTHER INFORMATION: Thr or Ser.
<220> FEATURE:
<221> NAME/KEY: Misc_feature
<222> LOCATION: (185)
<223> OTHER INFORMATION: Leu or Met.
<220> FEATURE:
<221> NAME/KEY: Misc_feature
<222> LOCATION: (192)
<223> OTHER INFORMATION: Ile or Val.
<220> FEATURE:
<221> NAME/KEY: Misc_feature
<222> LOCATION: (200)
<223> OTHER INFORMATION: Pro or Thr.
<220> FEATURE:
<221> NAME/KEY: Misc_feature
<222> LOCATION: (203)
<223> OTHER INFORMATION: Val or Ala.

<400> SEQUENCE: 4

```
Met Gln Thr Pro His Lys Glu His Leu Tyr Lys Leu Val Ile Gly
 1               5                  10                  15

Asp Leu Gly Val Gly Lys Thr Ser Ile Ile Lys Arg Tyr Val His Gln
                20                  25                  30

Asn Phe Ser Ser His Tyr Arg Ala Thr Ile Gly Val Asp Phe Ala Leu
            35                  40                  45

Lys Val Leu His Trp Asp Pro Glu Thr Val Val Arg Leu Gln Leu Trp
    50                  55                  60

Asp Ile Ala Gly Gln Glu Arg Phe Gly Asn Met Thr Arg Val Tyr Tyr
65                  70                  75                  80

Arg Glu Ala Met Gly Ala Phe Ile Val Phe Asp Val Thr Arg Pro Ala
                85                  90                  95

Thr Phe Glu Ala Val Ala Lys Trp Lys Asn Asp Leu Asp Ser Lys Leu
            100                 105                 110

Xaa Leu Pro Asn Gly Lys Pro Val Ser Val Leu Leu Ala Asn Lys
    115                 120                 125

Cys Asp Gln Gly Lys Asp Val Leu Met Asn Asn Gly Leu Lys Met Asp
130                 135                 140

Gln Phe Cys Lys Glu His Gly Phe Val Gly Trp Phe Glu Thr Ser Ala
145                 150                 155                 160
```

```
Lys Glu Asn Ile Asn Ile Asp Glu Ala Ser Arg Cys Leu Val Lys His
            165                 170                 175

Ile Leu Ala Asn Glu Cys Asp Leu Xaa Glu Ser Ile Glu Pro Asp Xaa
            180                 185                 190

Val Lys Pro His Leu Thr Ser Xaa Lys Val Xaa Ser Cys Ser Gly Cys
        195                 200                 205

Ala Lys Ser
    210

<210> SEQ ID NO 5
<211> LENGTH: 636
<212> TYPE: DNA
<213> ORGANISM: Mus musculus

<400> SEQUENCE: 5
```

| | | | | | | | | | | | | | | | | |
|---|---|---|---|---|---|---|---|---|---|---|---|---|---|---|---|---|
| atg cag aca cct cac aag gag cac ctg tac aag ctg ctg gtg atc ggc | | | | | | | | | | | | | | | | 48 |
| Met Gln Thr Pro His Lys Glu His Leu Tyr Lys Leu Leu Val Ile Gly | | | | | | | | | | | | | | | | |
| 1 | | | 5 | | | | | 10 | | | | | 15 | | | |

```
gac ctg ggt gtg ggc aag acc agc att atc aag cgc tat gtg cac caa      96
Asp Leu Gly Val Gly Lys Thr Ser Ile Ile Lys Arg Tyr Val His Gln
            20                  25                  30 aac ttc tcc tcg cac tac cgg gcc acc att ggt gtg gac ttc gcg ctg     144
Asn Phe Ser Ser His Tyr Arg Ala Thr Ile Gly Val Asp Phe Ala Leu
        35                  40                  45 aag gtg ctc cac tgg gac cca gag acg gtg gtg cgc ttg cag ctc tgg     192
Lys Val Leu His Trp Asp Pro Glu Thr Val Val Arg Leu Gln Leu Trp
    50                  55                  60 gac att gct ggt caa gaa aga ttt gga aac atg aca aga gtt tat tac     240
Asp Ile Ala Gly Gln Glu Arg Phe Gly Asn Met Thr Arg Val Tyr Tyr
65                  70                  75                  80 cgg gaa gct atg ggg gca ttt att gtt ttt gat gtc acc aga cca gcc     288
Arg Glu Ala Met Gly Ala Phe Ile Val Phe Asp Val Thr Arg Pro Ala
                85                  90                  95 aca ttt gaa gcc gtg gca aag tgg aaa aat gat ttg gac tca aag tta     336
Thr Phe Glu Ala Val Ala Lys Trp Lys Asn Asp Leu Asp Ser Lys Leu
            100                 105                 110 acg ctc cct aat ggt aag cca gtg tca gtg gtt ctg ttg gcc aac aaa     384
Thr Leu Pro Asn Gly Lys Pro Val Ser Val Val Leu Leu Ala Asn Lys
        115                 120                 125 tgt gac caa ggg aag gat gtg ctt atg aac aat gga ctc aag atg gac     432
Cys Asp Gln Gly Lys Asp Val Leu Met Asn Asn Gly Leu Lys Met Asp
    130                 135                 140 cag ttc tgc aag gag cat ggc ttc gta gga tgg ttt gaa aca tca gcc     480
Gln Phe Cys Lys Glu His Gly Phe Val Gly Trp Phe Glu Thr Ser Ala
145                 150                 155                 160 aag gaa aac ata aac att gat gaa gcc tca aga tgc ctg gtc aag cac     528
Lys Glu Asn Ile Asn Ile Asp Glu Ala Ser Arg Cys Leu Val Lys His
                165                 170                 175 ata ctt gca aat gag tgt gac ctc cta gag tct ata gaa ccg gac att     576
Ile Leu Ala Asn Glu Cys Asp Leu Leu Glu Ser Ile Glu Pro Asp Ile
            180                 185                 190 gtg aag ccc cat ctc aca tcg ccc aag gtt gtc agc tgc tct ggc tgt     624
Val Lys Pro His Leu Thr Ser Pro Lys Val Val Ser Cys Ser Gly Cys
        195                 200                 205 gcc aaa tcc tag                                                     636
Ala Lys Ser
    210

<210> SEQ ID NO 6
```

―continued

```
<211> LENGTH: 636
<212> TYPE: DNA
<213> ORGANISM: Homo sapiens

<400> SEQUENCE: 6 atg cag aca cct cac aag gag cac ctg tac aag ttg ctg gtg att ggc      48
Met Gln Thr Pro His Lys Glu His Leu Tyr Lys Leu Leu Val Ile Gly
 1               5                  10                  15 gac ctg ggc gtg ggg aag acc agt atc atc aag cgc tac gtg cac cag      96
Asp Leu Gly Val Gly Lys Thr Ser Ile Ile Lys Arg Tyr Val His Gln
             20                  25                  30 aac ttc tct tcg cac tac cgg gcc aca atc ggc gtg gac ttc gcg ctc     144
Asn Phe Ser Ser His Tyr Arg Ala Thr Ile Gly Val Asp Phe Ala Leu
         35                  40                  45 aag gtg ctc cac tgg gac ccg gag act gtg gtg cgc ctg cag ctc tgg     192
Lys Val Leu His Trp Asp Pro Glu Thr Val Val Arg Leu Gln Leu Trp
     50                  55                  60 gat atc gca ggt caa gaa aga ttt gga aac atg acg agg gtc tat tac     240
Asp Ile Ala Gly Gln Glu Arg Phe Gly Asn Met Thr Arg Val Tyr Tyr
 65                  70                  75                  80 cga gaa gct atg ggt gca ttt att gtc ttc gat gtc acc agg cca gcc     288
Arg Glu Ala Met Gly Ala Phe Ile Val Phe Asp Val Thr Arg Pro Ala
                 85                  90                  95 aca ttt gaa gca gtg gca aag tgg aaa aat gat ttg gac tcc aag tta     336
Thr Phe Glu Ala Val Ala Lys Trp Lys Asn Asp Leu Asp Ser Lys Leu
            100                 105                 110 agt ctc cct aat ggc aaa ccg gtt tca gtg gtt ttg ttg gcc aac aaa     384
Ser Leu Pro Asn Gly Lys Pro Val Ser Val Val Leu Leu Ala Asn Lys
        115                 120                 125 tgt gac cag ggg aag gat gtg ctc atg aac aat ggc ctc aag atg gac     432
Cys Asp Gln Gly Lys Asp Val Leu Met Asn Asn Gly Leu Lys Met Asp
    130                 135                 140 cag ttc tgc aag gag cac ggt ttc gta gga tgg ttt gaa aca tca gca     480
Gln Phe Cys Lys Glu His Gly Phe Val Gly Trp Phe Glu Thr Ser Ala
145                 150                 155                 160 aag gaa aat ata aac att gat gaa gcc tcc aga tgc ctg gtg aaa cac     528
Lys Glu Asn Ile Asn Ile Asp Glu Ala Ser Arg Cys Leu Val Lys His
                165                 170                 175 ata ctt gca aat gag tgt gac cta atg gag tct att gag ccg gac gtc     576
Ile Leu Ala Asn Glu Cys Asp Leu Met Glu Ser Ile Glu Pro Asp Val
            180                 185                 190 gtg aag ccc cat ctc aca tca acc aag gtt gcc agc tgc tct ggc tgt     624
Val Lys Pro His Leu Thr Ser Thr Lys Val Ala Ser Cys Ser Gly Cys
        195                 200                 205 gcc aaa tcc tag                                                     636
Ala Lys Ser
    210

<210> SEQ ID NO 7
<211> LENGTH: 28
<212> TYPE: PRT
<213> ORGANISM: Mus musculus

<400> SEQUENCE: 7

Phe Leu Cys Leu Glu Arg Asn Ala Lys Met Lys Val Cys Phe Cys Ile
 1               5                  10                  15

Leu Lys Thr Ser Leu Val Ile Leu Leu Phe Glu Gly
             20                  25

<210> SEQ ID NO 8
<211> LENGTH: 303
```

```
<212> TYPE: DNA
<213> ORGANISM: Mus musculus

<400> SEQUENCE: 8
gaattcgcgg ccgctac ttt ttg tgt ttg gaa cgg aat gca aag atg aag        50
                    Phe Leu Cys Leu Glu Arg Asn Ala Lys Met Lys
                     1               5                  10 gtc tgt ttc tgt att ctt aag aca tct ttg gtt att tta ctt ttt gaa      98
Val Cys Phe Cys Ile Leu Lys Thr Ser Leu Val Ile Leu Leu Phe Glu
            15                  20                  25 ggt tgatactgta aaagaataaa ccacaaattg attgggaaca tcatttcaag           151
Gly aagtccctgc tcctccacat tgtttttgcc gatttgcaca ttaaatgact cttccctcaa    211
ttctgtctta agaggcaaga gggtagggt ttacacgtag gcagttgggt tttttaaggg     271 cccctttta ataactgagc ggccgcgaat tc                                   303

<210> SEQ ID NO 9
<211> LENGTH: 22
<212> TYPE: PRT
<213> ORGANISM: Mus musculus

<400> SEQUENCE: 9

Ile Arg Gly Arg Cys Ser Phe Leu Val Phe Thr Ser Ser Cys Leu Ile
 1               5                  10                  15

Leu Val Phe Phe Ser Ser
            20

<210> SEQ ID NO 10
<211> LENGTH: 218
<212> TYPE: DNA
<213> ORGANISM: Mus musculus

<400> SEQUENCE: 10 ga att cgc ggc cgc tgc tcc ttt ttg gtt ttc aca agc agc tgc ttg att    50
   Ile Arg Gly Arg Cys Ser Phe Leu Val Phe Thr Ser Ser Cys Leu Ile
    1               5                  10                  15 tta gtg ttc ttt tct tca tagtgctgta ctgacgactg cagtgaagtt atttcttctt  108
Leu Val Phe Phe Ser Ser
            20 gtagggtttc ttgtttctct ttctgaattt tcatttcttg ctccaaatct tctattgtac    168 tgttttatt tgttaacttt tgatttagtt ctttcagcgg ccgcgaattc                 218

<210> SEQ ID NO 11
<211> LENGTH: 438
<212> TYPE: PRT
<213> ORGANISM: Mus musculus

<400> SEQUENCE: 11

Ser Leu Lys Arg Arg Leu Ala Ala Ala Leu Thr Ala Glu Pro Glu Pro
 1               5                  10                  15

Glu Arg Pro Leu Arg Val Pro Pro Pro Leu Ala Pro Arg Ala Ala
            20                  25                  30

Leu Ser Arg Asp Glu Ile Leu Arg Tyr Ser Arg Gln Leu Leu Pro
            35                  40                  45

Glu Leu Gly Val Arg Gly Gln Leu Arg Leu Ala Ala Ala Val Leu
        50                  55                  60

Val Val Gly Cys Gly Gly Leu Gly Cys Pro Leu Ala Gln Tyr Leu Ala
65                  70                  75                  80
```

| | | | | | | | | | | | |
|---|---|---|---|---|---|---|---|---|---|---|---|
| Ala | Ala | Gly | Val | Gly | Arg | Leu | Gly | Leu | Val | Asp | His | Asp | Val | Glu |
| | | | | 85 | | | | 90 | | | | 95 | | |

Thr Ser Asn Leu Ala Arg Gln Val Leu His Gly Glu Ala Gln Ala Gly
        100                 105                 110

Glu Ser Lys Ala Arg Ser Ala Ala Ala Leu Arg Arg Leu Asn Ser
        115                 120                 125

Ala Val Glu Cys Val Ala Tyr Pro Arg Ala Leu Ala Glu Asp Trp Ala
130                 135                 140

Leu Asp Leu Val Arg Gly Tyr Asp Val Ala Asp Cys Cys Asp Asn
145                 150                 155                 160

Val Pro Met Arg Tyr Leu Val Asn Asp Ala Cys Val Leu Ala Gly Arg
                165                 170                 175

Pro Leu Val Ser Ala Ser Ala Leu Arg Phe Glu Gly Gln Met Thr Val
                180                 185                 190

Tyr His His Asp Gly Gly Pro Cys Tyr Arg Cys Val Phe Pro Arg Pro
        195                 200                 205

Pro Pro Pro Glu Thr Val Thr Asn Cys Ala Asp Gly Val Leu Gly
210                 215                 220

Ala Val Pro Gly Val Leu Gly Cys Ala Gln Ala Leu Glu Val Leu Lys
225                 230                 235                 240

Ile Ala Ala Gly Leu Gly Ser Ser Tyr Ser Gly Ser Met Leu Leu Phe
                245                 250                 255

Asp Gly Leu Gly Gly His Phe Arg Arg Ile Arg Leu Arg Arg Arg
            260                 265                 270

Pro Asp Cys Val Val Cys Gly Gln Gln Pro Thr Val Thr Arg Leu Gln
            275                 280                 285

Asp Tyr Glu Ala Phe Cys Gly Ser Ser Ala Thr Asp Lys Cys Arg Ala
290                 295                 300

Leu Lys Leu Leu Cys Pro Glu Glu Arg Ile Ser Val Thr Asp Tyr Lys
305                 310                 315                 320

Arg Leu Leu Asp Ser Gly Ala Pro His Val Leu Leu Asp Val Arg Pro
                325                 330                 335

Gln Val Glu Val Asp Ile Cys Arg Leu Pro His Ser Leu His Ile Pro
            340                 345                 350

Leu Ser Gln Leu Glu Arg Arg Asp Ala Asp Ser Leu Lys Leu Leu Gly
            355                 360                 365

Ala Ala Leu Arg Lys Gly Lys Gln Glu Ser Gln Glu Gly Val Ala Leu
370                 375                 380

Pro Val Tyr Val Ile Cys Lys Leu Gly Asn Asp Ser Gln Lys Ala Val
385                 390                 395                 400

Lys Val Leu Gln Ser Leu Thr Ala Val Pro Glu Leu Asp Ser Leu Thr
                405                 410                 415

Val Gln Asp Ile Val Gly Gly Leu Met Ala Trp Ala Ala Lys Ile Asp
            420                 425                 430

Gly Thr Phe Pro Gln Tyr
        435

<210> SEQ ID NO 12
<211> LENGTH: 1353
<212> TYPE: DNA
<213> ORGANISM: Mus musculus

<400> SEQUENCE: 12
gaattcgcgg ccgctct tcg ctc aag cgg agg ctg gcc gcg gcc ctg aca gcc    53
                   Ser Leu Lys Arg Arg Leu Ala Ala Ala Leu Thr Ala -continued

|  | 1 |  |  |  | 5 |  |  |  |  | 10 |  |  |  |  |
|---|---|---|---|---|---|---|---|---|---|---|---|---|---|---|
| gag | ccg | gag | ccc | gag | cgt | ccg | ctc | cgg | gtc | ccg | ccg | ccg | ctg | gcg | 101 |
| Glu | Pro | Glu | Pro | Glu | Arg | Pro | Leu | Arg | Val | Pro | Pro | Pro | Leu | Ala |
|     |     | 15  |     |     |     |     | 20  |     |     |     |     | 25  |     |     |

| ccc | cgg | gcc | gcg | ctg | tcg | cgg | gac | gag | atc | ctc | cgc | tac | agc | cgc | cag | 149 |
| Pro | Arg | Ala | Ala | Leu | Ser | Arg | Asp | Glu | Ile | Leu | Arg | Tyr | Ser | Arg | Gln |
|     | 30  |     |     |     |     | 35  |     |     |     |     | 40  |     |     |     |     |

| cta | ctg | ctg | ccg | gag | ctg | ggc | gtg | cgc | ggg | cag | ctg | cgc | ctg | gcg | gcg | 197 |
| Leu | Leu | Leu | Pro | Glu | Leu | Gly | Val | Arg | Gly | Gln | Leu | Arg | Leu | Ala | Ala |
| 45  |     |     |     |     | 50  |     |     |     |     | 55  |     |     |     |     | 60  |

| gcg | gcg | gtg | ctc | gtg | gtg | ggc | tgc | ggg | ctg | ggc | tgc | ccg | ctg | gcg | 245 |
| Ala | Ala | Val | Leu | Val | Val | Gly | Cys | Gly | Leu | Gly | Cys | Pro | Leu | Ala |
|     |     |     |     | 65  |     |     |     |     | 70  |     |     |     |     | 75  |

| cag | tac | ctg | gcg | gcg | gcc | ggc | gta | ggc | agg | ctg | ggg | ctg | gtg | gac | cac | 293 |
| Gln | Tyr | Leu | Ala | Ala | Ala | Gly | Val | Gly | Arg | Leu | Gly | Leu | Val | Asp | His |
|     |     |     | 80  |     |     |     |     | 85  |     |     |     |     | 90  |     |     |

| gac | gtg | gtg | gag | acg | agc | aac | ctg | gcc | cgc | cag | gtc | ctg | cac | ggg | gag | 341 |
| Asp | Val | Val | Glu | Thr | Ser | Asn | Leu | Ala | Arg | Gln | Val | Leu | His | Gly | Glu |
|     |     | 95  |     |     |     |     | 100 |     |     |     |     | 105 |     |     |     |

| gcg | cag | gcc | ggc | gag | agc | aag | gct | cgc | tcg | gcg | gcc | gcg | gcg | ctg | cgc | 389 |
| Ala | Gln | Ala | Gly | Glu | Ser | Lys | Ala | Arg | Ser | Ala | Ala | Ala | Ala | Leu | Arg |
|     | 110 |     |     |     |     | 115 |     |     |     |     | 120 |     |     |     |     |

| cgt | ctc | aac | tcg | gcg | gtg | gag | tgc | gtg | gcg | tac | ccg | cgc | gcg | ctc | gcc | 437 |
| Arg | Leu | Asn | Ser | Ala | Val | Glu | Cys | Val | Ala | Tyr | Pro | Arg | Ala | Leu | Ala |
| 125 |     |     |     |     | 130 |     |     |     |     | 135 |     |     |     |     | 140 |

| gag | gac | tgg | gcg | ctc | gac | ctg | gtc | cgc | ggc | tac | gac | gtg | gtg | gca | gac | 485 |
| Glu | Asp | Trp | Ala | Leu | Asp | Leu | Val | Arg | Gly | Tyr | Asp | Val | Val | Ala | Asp |
|     |     |     |     | 145 |     |     |     |     | 150 |     |     |     |     | 155 |     |

| tgc | tgc | gac | aac | gtg | ccc | atg | cgc | tac | ctg | gtg | aac | gac | gcg | tgc | gtg | 533 |
| Cys | Cys | Asp | Asn | Val | Pro | Met | Arg | Tyr | Leu | Val | Asn | Asp | Ala | Cys | Val |
|     |     |     | 160 |     |     |     |     | 165 |     |     |     |     | 170 |     |     |

| ctg | gcc | ggc | cgg | ccg | cta | gtg | tcg | gcc | agc | gcg | ctg | cgc | ttc | gag | ggc | 581 |
| Leu | Ala | Gly | Arg | Pro | Leu | Val | Ser | Ala | Ser | Ala | Leu | Arg | Phe | Glu | Gly |
|     |     | 175 |     |     |     |     | 180 |     |     |     |     | 185 |     |     |     |

| cag | atg | acc | gtc | tac | cac | cac | gac | ggc | ggg | ccg | tgc | tac | cgc | tgc | gtg | 629 |
| Gln | Met | Thr | Val | Tyr | His | His | Asp | Gly | Gly | Pro | Cys | Tyr | Arg | Cys | Val |
|     | 190 |     |     |     |     | 195 |     |     |     |     | 200 |     |     |     |     |

| ttc | ccg | cgg | ccg | ccc | ccg | ccg | gag | aca | gtg | acc | aac | tgt | gca | gac | ggc | 677 |
| Phe | Pro | Arg | Pro | Pro | Pro | Pro | Glu | Thr | Val | Thr | Asn | Cys | Ala | Asp | Gly |
| 205 |     |     |     |     | 210 |     |     |     |     | 215 |     |     |     |     | 220 |

| ggc | gtg | ctc | gga | gcg | gtg | ccc | ggc | gtg | cta | ggc | tgc | gcg | cag | gcc | ctc | 725 |
| Gly | Val | Leu | Gly | Ala | Val | Pro | Gly | Val | Leu | Gly | Cys | Ala | Gln | Ala | Leu |
|     |     |     |     | 225 |     |     |     |     | 230 |     |     |     |     | 235 |     |

| gag | gtg | ctc | aag | atc | gcc | gcc | ggc | ctc | ggc | tcc | tcc | tac | agc | ggc | agc | 773 |
| Glu | Val | Leu | Lys | Ile | Ala | Ala | Gly | Leu | Gly | Ser | Ser | Tyr | Ser | Gly | Ser |
|     |     |     | 240 |     |     |     |     | 245 |     |     |     |     | 250 |     |     |

| atg | ctg | ctc | ttc | gac | ggc | ctc | ggg | ggc | cac | ttc | cgc | cgg | atc | cgg | ctg | 821 |
| Met | Leu | Leu | Phe | Asp | Gly | Leu | Gly | Gly | His | Phe | Arg | Arg | Ile | Arg | Leu |
|     |     | 255 |     |     |     |     | 260 |     |     |     |     | 265 |     |     |     |

| cgg | cgc | cgc | cgg | cct | gac | tgc | gtc | gtg | tgc | ggg | cag | cag | ccc | acc | gtg | 869 |
| Arg | Arg | Arg | Arg | Pro | Asp | Cys | Val | Val | Cys | Gly | Gln | Gln | Pro | Thr | Val |
|     | 270 |     |     |     |     | 275 |     |     |     |     | 280 |     |     |     |     |

| acc | cgc | ctg | cag | gac | tac | gag | gcc | ttc | tgc | ggc | tcg | tcg | gcc | acc | gac | 917 |
| Thr | Arg | Leu | Gln | Asp | Tyr | Glu | Ala | Phe | Cys | Gly | Ser | Ser | Ala | Thr | Asp |
| 285 |     |     |     |     | 290 |     |     |     |     | 295 |     |     |     |     | 300 |

| aag | tgc | cgc | gcc | ctg | aag | ctg | ctg | tgc | ccc | gag | gag | cgg | att | tct | gtg | 965 |
| Lys | Cys | Arg | Ala | Leu | Lys | Leu | Leu | Cys | Pro | Glu | Glu | Arg | Ile | Ser | Val |
|     |     |     |     | 305 |     |     |     |     | 310 |     |     |     |     | 315 |     |

| acc | gac | tac | aag | cgg | ctt | ctg | gat | tcc | ggg | gcg | ccc | cat | gtg | ttg | ctg | 1013 |

```
               Thr Asp Tyr Lys Arg Leu Leu Asp Ser Gly Ala Pro His Val Leu Leu
                       320                 325                 330 gac gtc cgg cct caa gta gag gtg gac atc tgt cgc ctg ccg cac tct            1061
Asp Val Arg Pro Gln Val Glu Val Asp Ile Cys Arg Leu Pro His Ser
        335                 340                 345 ctc cac atc cct ttg agt cag ttg gaa cgc agg gat gcg gac agc ctg            1109
Leu His Ile Pro Leu Ser Gln Leu Glu Arg Arg Asp Ala Asp Ser Leu
350                 355                 360 aaa ctc tta ggg gct gcc ctc cgg aaa ggg aag cag gag tcg cag gaa            1157
Lys Leu Leu Gly Ala Ala Leu Arg Lys Gly Lys Gln Glu Ser Gln Glu
365                 370                 375                 380 ggg gtt gct ctc ccg gtg tat gtg att tgc aaa ctg gga aac gac tcc            1205
Gly Val Ala Leu Pro Val Tyr Val Ile Cys Lys Leu Gly Asn Asp Ser
                385                 390                 395 cag aaa gct gtg aag gtc ctg cag tcc tta acg gca gtg ccg gag tta            1253
Gln Lys Ala Val Lys Val Leu Gln Ser Leu Thr Ala Val Pro Glu Leu
            400                 405                 410 gac tct tta act gtt cag gac atc gtg ggg gga ctc atg gcc tgg gcc            1301
Asp Ser Leu Thr Val Gln Asp Ile Val Gly Gly Leu Met Ala Trp Ala
        415                 420                 425 gcc aaa att gat ggg aca ttt cca cag tac tgagaggagc ggccgcgaat tc           1353
Ala Lys Ile Asp Gly Thr Phe Pro Gln Tyr
    430                 435

<210> SEQ ID NO 13
<211> LENGTH: 253
<212> TYPE: PRT
<213> ORGANISM: Mus musculus

<400> SEQUENCE: 13

Gly Ser Asp Asn Trp Ala Thr Val Met Phe Asn Gly Gln Lys Gly Leu
1               5                   10                  15

Val Pro Cys Asn Tyr Leu Glu Pro Val Glu Leu Arg Ile His Pro Gln
                20                  25                  30

Ser Gln Pro Gln Glu Asp Thr Ser Pro Glu Ser Asp Ile Pro Pro Pro
            35                  40                  45

Pro Asn Ser Ser Pro Gly Arg Leu Gln Leu Ser Pro Gly His Lys
        50                  55                  60

Gln Lys Glu Pro Lys Glu Leu Lys Leu Ser Val Pro Met Pro Tyr Met
65                  70                  75                  80

Leu Lys Val His Tyr Lys Tyr Thr Val Val Met Glu Thr Arg Leu Gly
                85                  90                  95

Leu Pro Tyr Ser Gln Leu Arg Asn Met Val Ser Lys Lys Leu Ala Leu
                100                 105                 110

Ser Pro Glu His Thr Lys Leu Ser Tyr Arg Arg Arg Asp Ser His Glu
            115                 120                 125

Leu Leu Leu Leu Ser Glu Glu Ser Met Lys Asp Ala Trp Gly Gln Val
130                 135                 140

Lys Asn Tyr Cys Leu Thr Leu Trp Cys Glu His Thr Val Gly Asp Gln
145                 150                 155                 160

Gly Leu Ile Asp Glu Pro Ile Gln Arg Glu Asn Ser Asp Ala Ser Lys
                165                 170                 175

Gln Thr Thr Glu Pro Gln Pro Lys Glu Gly Thr Gln Val Val Ala Ile
            180                 185                 190

Phe Ser Tyr Glu Ala Ala Gln Pro Glu Asp Leu Glu Phe Val Glu Gly
        195                 200                 205

Asp Val Ile Leu Val Leu Ser His Val Asn Glu Glu Trp Leu Glu Gly
```

```
                    210                 215                 220
Glu Cys Lys Gly Lys Val Gly Ile Phe Pro Lys Ala Phe Val Glu Gly
225                 230                 235                 240

Cys Ala Ala Lys Asn Leu Glu Gly Ile Pro Arg Glu Val
                245                 250

<210> SEQ ID NO 14
<211> LENGTH: 762
<212> TYPE: DNA
<213> ORGANISM: Mus musculus

<400> SEQUENCE: 14 ggc agt gat aac tgg gcc aca gtc atg ttc aat gga cag aag ggg ctt    48
Gly Ser Asp Asn Trp Ala Thr Val Met Phe Asn Gly Gln Lys Gly Leu
1                5                  10                  15 gtc ccc tgc aac tac ctg gag cca gtt gag ctt cgg att cac cct cag    96
Val Pro Cys Asn Tyr Leu Glu Pro Val Glu Leu Arg Ile His Pro Gln
                20                  25                  30 tcg cag ccc cag gaa gat acc tct cca gaa tcc gat att cca cca cct   144
Ser Gln Pro Gln Glu Asp Thr Ser Pro Glu Ser Asp Ile Pro Pro Pro
            35                  40                  45 cct aat tct agc ccc cca gga aga ctc cag ttg tca cca ggt cac aag   192
Pro Asn Ser Ser Pro Pro Gly Arg Leu Gln Leu Ser Pro Gly His Lys
        50                  55                  60 caa aaa gag ccc aag gaa ctg aag ctc agc gtg cct atg cct tac atg   240
Gln Lys Glu Pro Lys Glu Leu Lys Leu Ser Val Pro Met Pro Tyr Met
65                  70                  75                  80 ctc aag gtg cat tac aaa tac aca gtg gtc atg gag acg cgg ctt ggc   288
Leu Lys Val His Tyr Lys Tyr Thr Val Val Met Glu Thr Arg Leu Gly
                85                  90                  95 ctc ccc tac agc cag ctt cgg aac atg gtg tct aag aag ctg gcg ctc   336
Leu Pro Tyr Ser Gln Leu Arg Asn Met Val Ser Lys Lys Leu Ala Leu
                100                 105                 110 tcg cca gaa cac act aaa ctg agc tac cgg cgt cgg gac agc cac gag   384
Ser Pro Glu His Thr Lys Leu Ser Tyr Arg Arg Arg Asp Ser His Glu
            115                 120                 125 ctt ctg ctc ctg tcc gaa gaa agc atg aag gat gcc tgg ggc caa gtg   432
Leu Leu Leu Leu Ser Glu Glu Ser Met Lys Asp Ala Trp Gly Gln Val
        130                 135                 140 aaa aac tac tgc ctg act ctg tgg tgt gag cat acg gtg ggt gac caa   480
Lys Asn Tyr Cys Leu Thr Leu Trp Cys Glu His Thr Val Gly Asp Gln
145                 150                 155                 160 ggt ctt att gat gaa ccc ata caa agg gaa aac tca gac gcc agt aag   528
Gly Leu Ile Asp Glu Pro Ile Gln Arg Glu Asn Ser Asp Ala Ser Lys
                165                 170                 175 cag act acg gag cct cag cct aag gag ggg acc cag gtg gta gca atc   576
Gln Thr Thr Glu Pro Gln Pro Lys Glu Gly Thr Gln Val Val Ala Ile
                180                 185                 190 ttc agt tat gag gct gcc cag cca gaa gac ctg gaa ttt gtg gaa gga   624
Phe Ser Tyr Glu Ala Ala Gln Pro Glu Asp Leu Glu Phe Val Glu Gly
            195                 200                 205 gat gta atc ctg gta ctg tca cat gtg aat gaa gaa tgg ctg gaa ggg   672
Asp Val Ile Leu Val Leu Ser His Val Asn Glu Glu Trp Leu Glu Gly
        210                 215                 220 gag tgt aaa ggg aaa gtt ggc att ttc ccg aag gct ttt gtt gaa gga   720
Glu Cys Lys Gly Lys Val Gly Ile Phe Pro Lys Ala Phe Val Glu Gly
225                 230                 235                 240 tgt gca gcc aag aat ttg gaa ggc att ccc aga gaa gtc tag           762
Cys Ala Ala Lys Asn Leu Glu Gly Ile Pro Arg Glu Val
                245                 250
```

<210> SEQ ID NO 15
<211> LENGTH: 23
<212> TYPE: DNA
<213> ORGANISM: Artificial Sequence
<220> FEATURE:
<223> OTHER INFORMATION: Oligonucleotide designed to act as primer for
      amplifying cDNAs encoding mouse Rab proteins.

<400> SEQUENCE: 15
gggrrsagcr rcgtgggsaa rwc                                           23

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide designed to act as primer for
      amplifying cDNAs encoding mouse Rab proteins.
<220> FEATURE:
<221> NAME/KEY: Misc_feature
<222> LOCATION: (7)
<223> OTHER INFORMATION: i
<220> FEATURE:
<221> NAME/KEY: Misc_feature
<222> LOCATION: (13)
<223> OTHER INFORMATION: i

<400> SEQUENCE: 16
ttcytgnccw gcngtrtccc a                                             21

<210> SEQ ID NO 17
<211> LENGTH: 34
<212> TYPE: DNA
<213> ORGANISM: Artificial Sequence
<220> FEATURE:
<223> OTHER INFORMATION: Oligonucleotide designed to act as primer for
      amplifying cDNAs encoding human Rab proteins.

<400> SEQUENCE: 17
gcgaattcat gcttcttgga gactcgggcg tcgg                               34

<210> SEQ ID NO 18
<211> LENGTH: 35
<212> TYPE: DNA
<213> ORGANISM: Artificial Sequence
<220> FEATURE:
<223> OTHER INFORMATION: Oligonucleotide designed to act as primer for
      amplifying cDNAs encoding human Rab proteins.

<400> SEQUENCE: 18
gcgaattctc acacaaagga gcagcagctg gagcg                              35

<210> SEQ ID NO 19
<211> LENGTH: 34
<212> TYPE: DNA
<213> ORGANISM: Artificial Sequence
<220> FEATURE:
<223> OTHER INFORMATION: Oligonucleotide designed to act as primer for
      amplifying cDNAs encoding human Rab proteins.

<400> SEQUENCE: 19
gcgaattcat gcagacacct cacaaggagc acct                               34

<210> SEQ ID NO 20
<211> LENGTH: 35
<212> TYPE: DNA
<213> ORGANISM: Artificial Sequence -continued

```
<220> FEATURE:
<223> OTHER INFORMATION: Oligonucleotide designed to act as primer for
      amplifying cDNAs encoding human Rab proteins.

<400> SEQUENCE: 20
gcgaattcct aggatttggc acagccagag cagct                                    35
```

US 7,108,987 B2

FACTORS PARTICIPATING IN DEGRANULATION OF MAST CELLS, DNAS ENCODING THE SAME, METHOD OF SCREENING OF THESE FACTORS AND THE INHIBITORS

TECHNICAL FIELD

The present invention relates to novel factors involved in degranulation of mast cells and DNAs encoding them, antibodies against the factors, a method for assaying the factors in samples using the antibodies, a method for screening inhibitory substances of the factors and inhibitors containing a compound obtained by said method as an active ingredient. The present invention also relates to a therapeutic agent for a disease, in which degranulation of mast cells is involved, particularly allergic diseases, which contains an inhibitory substance of novel factors involved in the degranulation as an active ingredient.

BACKGROUND ART

When a biological organism is exposed to a foreign substance as an antigen, an IgE antibody specific to the antigen is produced in the body, and when the same antigen invades again, binding of IgE antibody with the IgE receptor formed on the surface of mast cells (also called mastocytes) stimulates extracellular release of the chemical mediators contained in granules in the mast cells, such as histamine, serotonin, platelet activating factor (PAF), heparin and the like. As a result, promotion of capillary permeability, bronchial smooth muscle constriction, increase in the secretion due to exocrine gland stimulation and the like are induced, which in turn leads to the onset of allergic inflammations such as anaphylactic shock, bronchial asthma, allergic rhinitis, hives, atopic dermatitis, drug hypersensitivity and the like.

Mast cells are responsible for not only the onset of allergic conditions caused by various chemical mediators released by stimulation of antigen and the like but also chronic allergic inflammation caused by the release of cytokines secondarily produced in the mast cells (M. K. Church & J. P. Caulfield, Chapter 5, pp. 5.1–5.12, Allergy, ed. S. T. Holgate et al., Gower Medical Publishing, London, UK (1993)).

Furthermore, the release of chemical mediators from the mast cells is induced not only by the action via IgE receptors but by various substances (IgG, complement, neuro-peptide, calcium ionophore, phorbol ester etc.). While the phenomenon of extracellular release of chemical mediators from the mast cells (degranulation) is considered to involve various factors such as cyclic AMP (cAMP), calcium ion, sodium ion, phosphoinositide metabolism, protein kinase C, phospholipase $A_2$, changes in membrane potential, and the like, but the detail thereof has not been elucidated (D. A. Kennerly & P. A. Duffy, Chapter 4, pp. 4.1–4.14, Allergy, ed, S. T. Holgate et al., Gower Medical Publishing, London, UK, (1993)).

As the therapeutic agent (hereinafter to be referred to as antiallergic agent) for allergic inflammations induced by these chemical mediators, either a pharmaceutical agent that suppresses the action of chemical mediators released from the mast cells, or a pharmaceutical agent that suppresses degranulation of the mast cells is currently used.

Adrenocorticosteroid drugs, which are typical antiallergic agents that suppress the action of chemical mediators, are effective but, due to the side effect associated with long-term administration, the development of a nonsteroidal antiallergic agent has been desired.

As nonsteroidal antiallergic agents, antihistamic agents, anti-leukotriene agents, anti-PAF agents, thromboxane $A_2$ synthase inhibitors and antagonists and the like are commercially available or under development, that block the action of chemical mediators released from mast cells, basophil and the like, activated by IgE antibody.

However, it is extremely difficult to create a pharmaceutical agent that basically suppresses degranulation of the mast cells. This is because the process of release of chemical mediators by mast cells stimulated by IgE antibody is extremely complicated and the mechanism of degranulation has not been clearly elucidated, as mentioned above. At present, pharmaceutical agents considered to have a degranulation suppressive action have been approved as antiallergic pharmaceutical products free of anti-histamic action and used for clinical treatment. Under the present situation, however, their action mechanisms are indefinite and the degranulation suppressive action is too weak to afford a superior treatment effect.

It is therefore an object of the present invention to provide a novel means for developing a pharmaceutical agent capable of basically suppressing the degranulation of the mast cells, and to provide a novel antiallergic agent that suppresses degranulation using this means.

DISCLOSURE OF THE INVENTION

The present inventors have constructed the following basic concept as regards the degranulation phenomenon of mast cells, which is the basic cause of the onset of uncomfortable conditions accompanying allergic inflammations and the like.

(1) The degranulation phenomenon is a reaction based on intracellular vesicular transport and a particular factor to be referred to as a "vesicular transport regulator" is involved.

(2) The functional expression of the particular vesicular transport regulator is closely related to a collaborative action of a different specific factor to be referred to as a "conjugate factor".

(3) Therefore, a substance that regulates or inhibits the action of this particular factor involved in the action mechanism can be clinically applied as a therapeutic agent for accurately controlling basic etiology that induces uncomfortable conditions.

(4) In other words, an antiallergic substance that basically suppresses the degranulation can be found by identifying this particular factor involved in the action mechanism (i.e., vesicular transport regulator and conjugate factor thereof) and screening a substance that regulates or inhibits its action.

It is therefore an object of the present invention to provide a vesicular transport regulator and a conjugate factor thereof, which are involved in degranulation of mast cells, and to provide a method for screening a substance that regulates or inhibits the function of these factors by constructing a cellular or cell-free assay system capable of interacting with these factors. A further object of the present invention is to provide, using such method, a therapeutic agent of allergic diseases in which promotion of degranulation of mast cells is involved.

Based on the above-mentioned concept, the present inventors took note of a Rab protein belonging to G protein having a function relating to the regulation of membrane transport in animal cells, as a factor to regulate the degranulation of mast cells.

In general terms, transport of intracellular substances to membranes is considered to involve G protein (also called a GTP binding protein) (P. Charvrier et al., Mol. Cell. Biol., vol. 10 No. 12, pp. 6578–6585 (1990); P. Charvrier et al., Cell, vol. 62, pp. 317–329 (1990)). For example, G protein is known to be involved in the process of translation and intracellular communication of the information of a ligand bound with the receptor on cell surfaces. In addition, the content of the information of the receptor to be intracellularly communicated via G protein is considered to be dependent on the kind of G protein involved in the communication, particularly the structure of its α subunit (D. A. Kennerly & P. A. Duffy, Chapter 4, pp. 4.1–4.14, Allergy, ed. S. T. Holgate et al., Gower Medical Publishing, London, UK (1993)). However, the whole picture of how the G protein is involved in the membrane transport is still unclear, and when it comes to the phenomenon of activation of mast cells by IgE receptor, whether or not G protein is in fact involved has not at all been reported in detail, much less what kind of G protein is involved.

More than 30 kinds of proteins belonging to the Rab family (sometimes to be simply referred to as Rab protein) have been heretofore reported as proteins that control intracellular vesicular transport for transporting substances from intracellular particular organelle to different organelle. For example, it has been reported that Rab3A protein is involved in transport of synaptic vesicles containing neurotransmitters (M. Matteoli et al., J. Cell Biol., vol. 115 No. 3, pp. 625–633 (1991)), Rab11 protein (O. Ullrich et al., J. Cell Biol., vol. 135 No. 4, pp. 913–924 (1996)) regulates recycling of endosome, and Rab5 protein regulates endocytosis (V. Rybin et al., Nature, vol. 383 No. 6597, pp. 266–269 (1996)), which suggests that each Rab protein is involved in particular function. In addition, these three kinds of Rab proteins specifically bind with rabphilin-3A (H. Shirataki et al., Mol. Cell Biol., vol. 13 No. 4, pp. 2061–2068, (1993)), rabphilin-11 (A. Mammoto et al., J. Biol. Chem., vol. 274 No. 36, pp. 25517–25524 (1999)) and rabaptin 5 (V. Rybin et al., Nature, vol. 383 No. 6597, pp. 266–269 (1996)), respectively, and reported to be coupled and involved in the expression of activity of Rab protein.

P. Chavrier et al. (Gene, vol. 112, pp. 261–264 (1992)) thoroughly searched for a gene encoding a novel protein classified into Rab protein or Rho protein from a cDNA library derived from mouse kidney and reported on 12 kinds of genes with the conclusion that there is no possibility of finding a novel Rab protein or Rho protein other than those reported.

However, with the dramatic progress in the genomics technology in recent years, new Rab genes are being found. For example, Incyte reported Rab genes such as Rab A, Rab B, Rab C, Rab D (WO 98/18942), SRAB (WO 98/42839), RABP-1, RABP-2 (WO 99/09182) and the like. Axys Pharmaceuticals searched for EST clones having homology with known Rab genes from human EST database, and identified the full-length sequences of the clones therefrom which had not been reported as Rab (WO 00/58464).

E. S. Masuda et al. (FEBS Lett., vol. 470, pp. 61–64 (2000)) further reported that cDNA of Rab37 was isolated as GTPase localized in secretory granule from a cDNA library derived from mouse mast cells.

However, a G protein (particularly Rab protein) or a gene thereof that in fact clearly regulates degranulation of mast cells has not been known, and the presence of a conjugate factor has not been known at all, either.

With the aim of identifying a Rab protein that in fact regulates degranulation of mast cells, the present inventors prepared a primer based on the sequence characteristic of a known Rab protein and conducted RT-PCR using, as a template, RNA prepared from cultured mast cells derived from mouse bone marrow cells. As a result, two kinds of cDNAs encoding novel Rab proteins were successfully cloned. Further, using an oligonucleotide corresponding to a partial base sequence of the mouse cDNAs as a primer, they cloned the corresponding human Rab protein genes from human cDNAs in the same manner as above. In addition, the present inventors successfully cloned cDNAs encoding novel conjugate factors that interact with these Rab proteins, by two-hybrid method using a yeast cell line (C. Chien et al., Proc. Natl. Acad. Sci. USA, vol. 88 No. 21, pp. 9578–9582 (1991)). Moreover, they have confirmed that recombinant Rab proteins obtained from cells transformed with expression vectors containing these cDNAs, and conjugate factors thereof, show an effect on the degranulation of mast cells, thereby demonstrating that these factors are regulatory factors involved in degranulation.

The present inventors have then established a method for screening a degranulation regulator inhibitory substance, which comprises bringing a candidate substance, that may inhibit the action of a degranulation regulator, into contact with a yeast cell line, into which a Rab protein gene and a gene of a conjugate factor thereof had been introduced by the two-hybrid method, and examining the effect on the interaction. In addition, they have established a cell-free assay system capable of screening a substance that inhibits interaction between the Rab protein and a conjugate factor thereof or the GTP binding activity of the Rab protein. Furthermore, they have demonstrated that a useful antiallergic agent can be created by such screening method, which resulted in the completion of the present invention.

Accordingly, the present invention provides the following.

[1] A protein of the following (a), (b) or (c):
(a) a protein having the amino acid sequence depicted in SEQ ID NO:1,
(b) a protein having an amino acid sequence which is the amino acid sequence of the above-mentioned (a), wherein one to several amino acids are substituted, deleted, inserted, added or modified, and capable of regulating degranulation of mast cells on its own or by interaction with one or more conjugate factors,
(c) a fragment of the protein of the above-mentioned (a), which is a protein capable of regulating degranulation of mast cells on its own or by interaction with one or more conjugate factors.

[2] A protein of the following (a), (b) or (c):
(a) a protein having the amino acid sequence depicted in SEQ ID NO:4,
(b) a protein having an amino acid sequence which is the amino acid sequence of the above-mentioned (a), wherein one to several amino acids are substituted, deleted, inserted, added or modified, and capable of regulating degranulation of mast cells on its own or by interaction with one or more conjugate factors,
(c) a fragment of the protein of the above-mentioned (a), which is a protein capable of regulating degranulation of mast cells on its own or by interaction with one or more conjugate factors.

[3] A protein of the following (a), (b) or (c):
(a) a protein having the amino acid sequence depicted in SEQ ID NO:7,
(b) a protein having an amino acid sequence which is the amino acid sequence of the above-mentioned (a), wherein one to several amino acids are substituted, deleted, inserted, added or modified, and capable of regulating degranulation of mast cells on its own or by interaction with the protein of the above-mentioned [1],
(c) a fragment of the protein of the above-mentioned (a), which is a protein capable of regulating degranulation of mast cells on its own or by interaction with the protein of the above-mentioned [1].

[4] A protein of the following (a), (b) or (c):
(a) a protein having the amino acid sequence depicted in SEQ ID NO:9,
(b) a protein having an amino acid sequence which is the amino acid sequence of the above-mentioned (a), wherein one to several amino acids are substituted, deleted, inserted, added or modified, and capable of regulating degranulation of mast cells on its own or by interaction with the protein of the above-mentioned [1],
(c) a fragment of the protein of the above-mentioned (a), which is a protein capable of regulating degranulation of mast cells on its own or by interaction with the protein of the above-mentioned [1].

[5] A protein of the following (a), (b) or (c):
(a) a protein having the amino acid sequence depicted in SEQ ID NO:11,
(b) a protein having an amino acid sequence which is the amino acid sequence of the above-mentioned (a), wherein one to several amino acids are substituted, deleted, inserted, added or modified, and capable of regulating degranulation of mast cells on its own or by interaction with the protein of the above-mentioned [1],
(c) a fragment of the protein of the above-mentioned (a), which is a protein capable of regulating degranulation of mast cells on its own or by interaction with the protein of the above-mentioned [1].

[6] A protein of the following (a), (b) or (c):
(a) a protein having the amino acid sequence depicted in SEQ ID NO:13,
(b) a protein having an amino acid sequence which is the amino acid sequence of the above-mentioned (a), wherein one to several amino acids are substituted, deleted, inserted, added or modified, and capable of regulating degranulation of mast cells on its own or by interaction with the protein of the above-mentioned [2],
(c) a fragment of the protein of the above-mentioned (a), which is a protein capable of regulating degranulation of mast cells on its own or by interaction with the protein of the above-mentioned [2].

[7] The protein of any of the above-mentioned [1]–[6], which is derived from a mammal, particularly a human or a mouse.

[8] A DNA encoding the protein of the above-mentioned [1], particularly, a DNA identified by the following (a), (b) or (c):
(a) a DNA having the base sequence depicted in SEQ ID NO:2 or 3,
(b) a DNA comprising a base sequence which is the base sequence of the above-mentioned (a), wherein one to several bases are substituted, deleted, inserted or added,
(c) a fragment of the DNA having the base sequence of the above-mentioned (a).

[9] A DNA encoding the protein of the above-mentioned [2], particularly, a DNA identified by the following (a), (b) or (c):
(a) a DNA having a base sequence depicted in SEQ ID NO:5 or 6,
(b) a DNA comprising a base sequence which is the base sequence of the above-mentioned (a), wherein one to several bases are substituted, deleted, inserted or added,
(c) a fragment of the DNA having the base sequence of the above-mentioned (a).

[10] A DNA encoding the protein of the above-mentioned [3], particularly, a DNA identified by the following (a), (b) or (c):
(a) a DNA having the base sequence consisting of base Nos. 18–104 of the base sequence depicted in SEQ ID NO:8,
(b) a DNA comprising a base sequence which is the base sequence of the above-mentioned (a), wherein one to several bases are substituted, deleted, inserted or added,
(c) a fragment of the DNA having the base sequence of the above-mentioned (a).

[11] A DNA encoding the protein of the above-mentioned [4], particularly, a DNA identified by the following (a), (b) or (c):
(a) a DNA having a base sequence consisting of base Nos. 18–68 of the base sequence depicted in SEQ ID NO:10,
(b) a DNA comprising a base sequence which is the base sequence of the above-mentioned (a), wherein one to several bases are substituted, deleted, inserted or added,
(c) a fragment of the DNA having the base sequence of the above-mentioned (a).

[12] A DNA encoding the protein of the above-mentioned [5], particularly, a DNA identified by the following (a), (b) or (c):
(a) a DNA having a base sequence consisting of base Nos. 18–1334 of the base sequence depicted in SEQ ID NO:12,
(b) a DNA comprising a base sequence which is the base sequence of the above-mentioned (a), wherein one to several bases are substituted, deleted, inserted or added,
(c) a fragment of the DNA having the base sequence of the above-mentioned (a).

[13] A DNA encoding the protein of the above-mentioned [6], particularly, a DNA identified by the following (a), (b) or (c):
(a) a DNA having the base sequence depicted in SEQ ID NO:14,
(b) a DNA comprising a base sequence which is the base sequence of the above-mentioned (a), wherein one to several bases are substituted, deleted, inserted or added,
(c) a fragment of the DNA having the base sequence of the above-mentioned (a).

[14] A DNA of any of the above-mentioned [8]–[13], which is derived from a mammal, particularly a human or a mouse.

[15] A recombinant vector containing the DNA of any of the above-mentioned [8]–[14].

[16] A transformant obtained by introducing the recombinant vector of the above-mentioned [15] into a host cell.

[17] A production method of the protein of any of the above-mentioned [1]–[7], which comprises harvesting the protein from a culture obtained by culturing the transformant of the above-mentioned [16].

[18] An antibody having a specific affinity for the protein of any of the above-mentioned [1]–[7].

[19] A reagent for assaying the protein of any of the above-mentioned [1]–[7] in a sample, which contains the antibody of the above-mentioned [18].

[20] A method for assaying the protein of any of the above-mentioned [1]–[7] in a sample, based on an antigen-antibody reaction of the antibody of the above-mentioned [18].

[21] A transformant obtained by introducing an expression vector comprising the DNA of the above-mentioned [8] (or [9]) in a form permitting expression as a fusion protein with a partial sequence of a protein that regulates expression of a reporter gene in a host cell, and an expression vector comprising the DNA of the above-mentioned [10]–[12] (or [13]) in a form permitting expression as a fusion protein with a different partial sequence of said protein (provided that said two partial sequences restore a function to regulate expression of the reporter gene only when the obtained two fusion proteins interact) into a host cell, particularly such a transformant wherein said two partial sequences are a DNA binding domain and an active domain of a transcription factor.

[22] A screening method of a substance capable of inhibiting degranulation of mast cells, which comprises
(1) culturing the transformant of the above-mentioned [21] in culture medium both in the presence and absence of a test substance, and
(2) comparing an expression of a reporter gene.

[23] A screening method of a substance capable of inhibiting degranulation of mast cells, which comprises
(1) bringing the protein of the above-mentioned [1] or [2] in contact with GTP both in the presence and absence of a test substance, and
(2) comparing binding of GTP to the protein.

[24] A screening method of a substance capable of inhibiting degranulation of mast cells, which comprises the following steps performed both in the presence and absence of a test substance:
(1) a step of forming a complex by bringing the protein of the above-mentioned [1] (or [2]) in contact with the protein of any of the above-mentioned [3]–[5] (or [6])
(2) a step of binding GTP to the protein of the above-mentioned [1] (or [2]) (the order of steps (1) and (2) may be reversed or simultaneous)
(3) a step of assaying a complex of the protein of the above-mentioned [1] (or [2]) bound with GTP and the protein of any of the above-mentioned [3]–[5] (or [6]) (provided that any component selected from the group consisting of the protein of the above-mentioned [1] (or [2]), the protein of any of the above-mentioned [3]–[5] (or [6]) and GTP has been labeled).

[25] A substance that inhibits degranulation of mast cells, which is obtained by the method of any of the above-mentioned [22]–[24], particularly such inhibitory substance represented by the formula [I] or [II]:

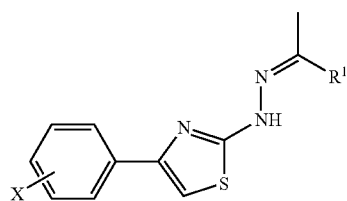

wherein $R^1$ is a hydrogen atom or a straight chain or branched chain alkyl group having 1 to 4 carbon atoms, and X is a hydrogen atom, a straight chain or branched chain alkyl group having 1 to 4 carbon atoms, a hydroxyl group or a phenyl group

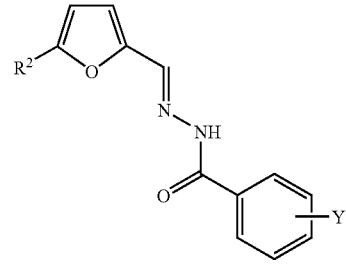

wherein $R^2$ is a hydrogen atom or a nitro group, and Y is a halogen atom, a straight chain or branched chain alkyl group having 1 to 4 carbon atoms or a hydroxyl group.

[26] An inhibitor of degranulation of mast cells, which comprises the inhibitory substance of the above-mentioned [25] as an active ingredient.

[27] A therapeutic agent of an allergic disease involving promotion of degranulation of mast cells, which comprises the inhibitory substance of the above-mentioned [25].

BEST MODE FOR EMBODYING THE INVENTION

The present invention provides two kinds of novel Rab proteins capable of regulating degranulation of mast cells. These Rab proteins each can regulate degranulation of mast cells by interacting with a particular conjugate factor to be mentioned below. However, an exogenous Rab protein can suppressively regulate degranulation of mast cells on its own.

A first Rab protein of the present invention preferably consists of the amino acid sequence depicted in SEQ ID NO:1, and may be such amino acid sequence wherein one to several amino acids of said amino acid sequence are substituted, deleted, inserted, added or modified, or may be a fragment of a protein consisting of said amino acid sequence, as long as it can regulate degranulation of mast cells on its own or by interaction with one or more conjugate factors.

A second Rab protein of the present invention preferably consists of the amino acid sequence depicted in SEQ ID NO:4, and may be such amino acid sequence wherein one to several amino acids of said amino acid sequence are substituted, deleted, inserted, added or modified, or may be a fragment of a protein consisting of said amino acid sequence, as long as it can regulate degranulation of mast cells on its own or by interaction with one or more conjugate factors.

Proteins are generally folded in a compact shape and it is often the case that a partial amino acid sequence in the protein plays an important role in binding proteins to each other. In the present invention, therefore, the entire amino acid sequence depicted in SEQ ID NO:1 or SEQ ID NO:4 need not be included, as long as it has an activity to bind with a conjugate factor, or as long as it can regulate degranulation of mast cells on its own or by interaction with one or more conjugate factors, and a fragment of said protein may be used.

The Rab protein fragment of the present invention, or a fragment having a binding activity with a conjugate factor, can be obtained by, for example, purifying a peptide fragment of a Rab protein digested by endopeptidase and examining an inhibitory action on the binding between the Rab protein and a conjugate factor. When, for example, substitution, deletion or insertion of the amino acids in the Rab protein of the present invention by genetic engineering results in the loss of the activity of the mutated Rab protein to bind with a conjugate factor, a fragment having a binding activity with a conjugate factor can be obtained from the fragments containing a mutation introduction site (substituted amino acid residue, deleted amino acids (sequence) and amino acid sequence destroyed by the insertion etc.). Because, in general, proteins are considered to expose a hydrophilic region thereof on a molecular surface, a fragment having the binding activity can be also obtained by assuming the hydrophilic and hydrophobic regions from the amino acid sequence by the method of, for example, D. Eisenberg et al. (Proc. Natl. Acad. Sci. USA, vol. 81, pp. 140–144 (1984)).

The Rab protein of the present invention is not particularly limited as to its origin, as long as it has the abovementioned characteristics. Therefore, it encompasses those derived from naturally occurring biological organisms, and those derived from natural or artificial mutants, or transformant obtained by introducing a gene encoding a heterologous (i.e., exogenous) Rab protein into a host. Preferably, Rab proteins derived from mammals such as human, bovine, pig, horse, monkey, sheep, goat, dog, cat, rabbit, mouse, rat, guinea pig and the like are exemplified. Particularly preferably, it is derived from a human or mouse.

The first Rab protein derived from human is preferably exemplified by, but not limited to, one having a sequence which is the sequence depicted in SEQ ID NO:1, wherein amino acid Nos. 45, 115, 138, 165 and 167 are Val, Met, Leu, His and Ala, respectively. The first Rab protein derived from mouse is preferably exemplified by, but not limited to, one having a sequence which is the sequence depicted in SEQ ID NO:1, wherein amino acid Nos. 45, 115, 138, 165 and 167 are Ala, Val, Met, Arg and Pro, respectively.

The second Rab protein derived from human is preferably exemplified by, but not limited to, one having a sequence which is the sequence depicted in SEQ ID NO:4, wherein amino acid Nos. 113, 185, 192, 200 and 203 are Ser, Met, Val, Thr and Ala, respectively. The second Rab protein derived from mouse is preferably exemplified by, but not limited to, one having a sequence which is the sequence depicted in SEQ ID NO:4, wherein amino acid Nos. 113, 185, 192, 200 and 203 are Thr, Leu, Ile, Pro and Val, respectively.

The Rab protein of the present invention may comprise a sugar chain added thereto. When, for example, the amino acid sequence comprises Asn-X-Thr(Ser) (X is an optional amino acid), the sugar chain may have been added (Z. Khalkhall & R. D. Marshall, Biochem. J., vol. 146, pp. 299–307 (1975)).

The Rab proteins of the present invention may have different molecular weights depending on the difference in amino acid composition and sugar chain addition. As a polypeptide chain without addition of sugar chain, the first Rab protein preferably has a molecular weight of about 21.5 kDa, and the second Rab protein has a molecular weight of about 23.8 kDa (each theoretical value).

The Rab protein of the present invention can be obtained by (1) a method comprising extraction and purification using, as a starting material, a tissue or cell capable of producing the protein, (2) a chemical synthesis method or (3) a method comprising purification from a cell engineered to express the protein by a gene recombination technique.

The mast cell is a cell in a tissue that corresponds to basophils in blood, and is present in the vicinity of blood vessels in any tissue in the body. Particularly, it is distributed in a great number immediately under the skin, airway, mucosa of gastrointestinal tract and the like. The mast cell that plays an important role in the induction of allergic reactions is a mucosal-type mast cell. In recent years, a method for differentiating mast cells from mouse bone marrow cells has been reported (T. Nakano et al., J. Exp. Med., vol. 162, pp. 1025–1043 (1987)), thus establishing a method for preparation of a large amount of mucosal-type mast cells. In addition, there is a recent report on the method for differentiating mast cells from hematopoietic stem cells derived from human bone marrow cells or cord blood cells (H. Saito et al., Int. Arch. Allergy Immunol., vol. 107, No. 1–3, pp. 63–65 (1995). Therefore, isolation and purification of this protein from natural Rab protein-producing tissues can be performed as shown in the following.

Culture mast cells differentiated by the aforementioned method from hematopoietic stem cells derived from bone marrow cells or cord blood cells of mammals such as human, mouse, rat and the like are homogenized in a suitable extraction buffer and the cell extract is obtained by ultrasonication, surfactant treatment and the like, which is then purified by a suitable combination of separation techniques conventionally used for separation and purification of proteins. Examples of such separation technique include a method utilizing difference in solubility, such as salting out, solvent precipitation and the like, a method utilizing difference in molecular weight, such as dialysis, ultrafiltration, gel filtration, non-denaturing polyacrylamide gel electrophoresis (PAGE), sodium dodecyl sulfate—polyacrylamide gel electrophoresis (SDS-PAGE) and the like, a method utilizing charge, such as ion exchange chromatography, hydroxyapatite chromatography and the like, a method utilizing specific affinity, such as affinity chromatography and the like, a method utilizing difference in hydrophobicity, such as reverse high performance liquid chromatography and the like, a method utilizing difference in isoelectric point, such as isoelectric focusing and the like, and the like.

Production of Rab protein by chemical synthesis can be done by, for example, synthesizing the entirety or a part of the sequence based on the amino acid sequence depicted in SEQ ID NO:1 or SEQ ID NO:4 using a peptide synthesizer, and renaturation of the obtained polypeptide under suitable renaturation conditions.

The Rab protein of the present invention can be preferably produced by cloning a DNA encoding the protein, and isolation and purification of the culture of a transformant containing an expression vector carrying the DNA.

Gene is generally cloned by the following method. First, the desired protein is partially or completely purified from the cells or tissues that produce the protein by the abovementioned method and the N terminal amino acid sequence thereof is determined by the Edman method. In addition, the amino acid sequence of the oligopeptide obtained by partially lysing the protein by a protease or chemical substance that specifically cleaves the peptide sequence is similarly determined by the Edman method. An oligonucleotide having a base sequence corresponding to the determined partial amino acid sequence is synthesized, and using this as a probe, a DNA encoding the protein is cloned by colony (or plaque) hybridization from a cDNA or genomic DNA library prepared from a cell or tissue that produces said protein.

Alternatively, the entirety or a part of the cDNA encoding the protein can be specifically amplified by RT-PCR using the above-mentioned oligonucleotide as a primer and RNA prepared from the cell or tissue that produces the protein as a template. When a partial sequence is obtained, a full-length cDNA can be cloned by colony (or plaque) hybridization in the same manner as above, using the amplified fragment as a probe.

When a number of genes belonging to the same superfamily are known, like the Rab protein of the present invention, an oligonucleotide to be used as a probe or primer can be synthesized based on a sequence showing conservability found by homology comparison with known gene group.

Alternatively, an antibody against said protein is prepared according to a conventional method using the entirety or a part of a completely or partially purified protein as an antigen, and a DNA encoding the protein can be cloned by the antibody screening method from a cDNA or genomic DNA library prepared from the cell or tissue that produces the protein.

When the gene of a protein having physiological function similar to that of the objective protein is known, a clone having homology to the base sequence of the known gene is searched from EST (Expressed Sequence Tag) clones of mammals such as human, mouse, rat and the like, which are registered on the database available to the public such as EMBL, GenBank and the like, a probe is prepared as mentioned above based on the base sequence of the extracted EST clone, and a DNA encoding the protein can be cloned according to the colony (or plaque) hybridization method. In the case of the Rab protein of the present invention, an EST clone, which is a fragment of cDNA encoding the objective Rab protein, can be found by a homology search to base sequences of various Rab proteins, derived from mammals such as human, mouse, rat and the like.

Alternatively, a RACE (Rapid Amplification of cDNA End) method (M. A. Frohman et al., Proc. Natl. acad. Sci. USA, vol. 85, pp. 8998–9002 (1988)) can be used as a method for obtaining a cDNA clone more quickly and more conveniently. To be specific, an EST clone corresponding to a part of a Rab protein gene is extracted as mentioned above, each oligonucleotide homologous to a partial base sequence of a sense chain and an anti-sense chain of the EST clone is synthesized, a 5' and 3' RACE reactions are performed using each oligonucleotide and a suitable adaptor primer as a pair of PCR primers, and each amplification fragment is ligated by a method using a restriction enzyme and a ligase, and the like to give a full length cDNA clone.

The base sequence of the DNA obtained as mentioned above can be determined using a known sequencing technique such as Maxam-Gilbert method, dideoxy termination method and the like.

The DNA encoding the first Rab protein of the present invention is preferably a DNA encoding the amino acid sequence depicted in SEQ ID NO:1, an amino acid sequence which is said amino acid sequence wherein one to several amino acids are deleted, substituted, inserted, added or modified, or a fragment of the amino acid sequence (provided that a protein consisting of the mutated amino acid sequence or the fragment has a physiological activity capable of regulating degranulation of mast cells on its own or by interaction with one or more conjugate factors). More preferably, the DNA encoding the first Rab protein of the present invention is preferably a DNA having a base sequence depicted in SEQ ID NO:2 or 3, a DNA comprising a base sequence which is said base sequence wherein one to several bases are deleted, substituted, inserted or added, or a fragment of the DNA having the base sequence (provided that a protein encoded by the mutated base sequence or the fragment has a physiological activity capable of regulating degranulation of mast cells on its own or by interaction with one or more conjugate factors).

The DNA encoding the second Rab protein of the present invention is preferably a DNA encoding the amino acid sequence depicted in SEQ ID NO:4, an amino acid sequence which is said amino acid sequence wherein one to several amino acids are deleted, substituted, inserted, added or modified, or a fragment of the amino acid sequence (provided that a protein consisting of the mutated amino acid sequence or the fragment has a physiological activity capable of regulating degranulation of mast cells on its own or by interaction with one or more conjugate factors). More preferably, the DNA encoding the second Rab protein of the present invention is preferably a DNA having the base sequence depicted in SEQ ID NO:5 or 6, a DNA comprising a base sequence which is said base sequence wherein one to several bases are deleted, substituted, inserted or added, or a fragment of the DNA having a base sequence which is said base sequence (provided that a protein encoded by the mutated base sequence or the fragment has a physiological activity capable of regulating degranulation of mast cells on its own or by interaction with one or more conjugate factors).

The DNA encoding the first Rab protein of the present invention can be also chemically synthesized entirely based on the base sequence depicted in SEQ ID NO:2 or 3, according to, for example, the method of Y. A. Ovchinnikov et al. (Gene, vol. 31, pp. 65–78 (1984)). The DNA encoding the second Rab protein of the present invention can be chemically synthesized entirely likewise based on the base sequence depicted in SEQ ID NO:5 or 6.

The present invention also provides conjugate factors capable of regulating degranulation of mast cells by interaction with the above-mentioned two kinds of the Rab proteins of the present invention. When these conjugate factors are provided exogenously into the mast cell, they can suppressively regulate the degranulation on its own.

A first conjugate factor capable of specific interaction with the first Rab protein of the present invention is preferably a protein having the amino acid sequence depicted in SEQ ID NO:7. As long as it can regulate the degranulation of mast cells by interaction with the Rab protein, however, it may have an amino acid sequence which is said amino acid sequence wherein one to several amino acids are substituted, deleted, inserted, added or modified, or may be a fragment of the protein having said amino acid sequence.

A second conjugate factor capable of specific interaction with the first Rab protein of the present invention is preferably a protein having the amino acid sequence depicted in SEQ ID NO:9. As long as it can regulate the degranulation of mast cells on its own or by interaction with the Rab protein, however, it may have an amino acid sequence which is said amino acid sequence wherein one to several amino acids are substituted, deleted, inserted, added or modified, or may be a fragment of a protein having said amino acid sequence.

A third conjugate factor capable of specific interaction with the first Rab protein of the present invention is preferably a protein having the amino acid sequence depicted in SEQ ID NO:11. As long as it can regulate the degranulation of mast cells by interaction with the Rab protein, however, it may have an amino acid sequence which is said amino acid sequence wherein one to several amino acids are substituted, deleted, inserted, added or modified, or may be a fragment of the protein having said amino acid sequence.

A conjugate factor capable of specific interaction with the second Rab protein of the present invention is preferably a protein having the amino acid sequence depicted in SEQ ID NO:13. As long as it can regulate the degranulation of mast cells on its own or by interaction with the Rab protein, however, it may have an amino acid sequence which is said amino acid sequence wherein one to several amino acids are substituted, deleted, inserted, added or modified, or may be a fragment of the protein having said amino acid sequence.

As mentioned above, proteins are generally folded in a compact shape and a partial amino acid sequence in the protein often plays an important role in binding proteins to each other. In the present invention, therefore, the entire amino acid sequence depicted in SEQ ID NO:7, 9, 11 or 13 need not be included, as long as it has an activity to bind with the Rab protein, or as long as it can regulate degranulation of mast cells on its own or by interaction with Rab protein, and a fragment of said protein may be used.

The fragment of the conjugate factor of the present invention can be obtained by the same strategy as mentioned above with regard to the method for obtaining a fragment of the Rab protein.

The conjugate factor of the present invention is not particularly limited as to its origin, as long as it has the above-mentioned characteristics. Therefore, it encompasses those derived from naturally occurring biological organisms, and those derived from natural or artificial mutants, or transformant obtained by introducing a gene encoding a heterologous (i.e., exogenous) Rab protein into a host. Preferably, conjugate factors derived from mammals such as human, bovine, pig, horse, monkey, sheep, goat, dog, cat, rabbit, mouse, rat, guinea pig and the like are exemplified. Particularly preferably, it is derived from a human or mouse.

The conjugate factor capable of specific interaction with the first Rab protein of the present invention may have a different molecular weight depending on the difference in amino acid composition and sugar chain addition. As a polypeptide chain without addition of sugar chain, for example, the first conjugate factor preferably has a molecular weight of about 3.2 kDa, the second conjugate factor has a molecular weight of about 1.9 kDa and the third conjugate factor has a molecular weight of about 47.0 kDa (each theoretical value).

The conjugate factor capable of specific interaction with the second Rab protein of the present invention may have a different molecular weight depending on the difference in amino acid composition and sugar chain addition. As a polypeptide chain without addition of sugar chain, it preferably has, for example, a molecular weight of about 28.5 kDa (theoretical value).

The conjugate factor capable of specific interaction with the Rab protein of the present invention can be obtained in the same manner as described for the above-mentioned Rab protein by (1) a method comprising extraction and purification using a tissue or cell capable of producing the protein as a starting material, (2) a chemical synthesis method or (3) a method comprising purification from a cell engineered to express the protein by gene recombination technique.

Preferably, however, the conjugate factor is obtained utilizing the interaction property with the corresponding Rab protein and by the technique called a two-hybrid system, by cloning a cDNA encoding it, culturing a host cell transformed with an expression vector containing the obtained cDNA clone and isolating and purifying the conjugate factor from the obtained culture.

That is, a cDNA encoding the desired conjugate factor can be obtained by introducing, into a host cell, an expression vector comprising a DNA encoding the corresponding Rab protein in a form permitting expression as a fusion protein with a partial sequence of a protein that regulates expression of a reporter gene (e.g., gene encoding β-galactosidase, β-glucuronidase, luciferase etc. and a gene imparting resistance to a pharmaceutical agent such as kanamycin, hygromycin, bialaphos and the like, or a gene that supplements amino acid nutrition requirements (histidine synthase, leucine synthase etc.), and an expression vector comprising each clone of a cDNA library prepared from a tissue or cell (e.g., culture mast cell differentiated as mentioned above from hematopoietic stem cells derived from bone marrow cells or cord blood cells of mammals such as human, mouse, rat and the like) that produces a conjugate factor, in a form permitting expression as a fusion protein with a different partial sequence of said expression regulatory protein, (provided that said two partial sequences restore a function to regulate expression of the reporter gene only when the obtained two fusion proteins interact), to give a transformant cell, screening cells that highly expresses the reporter gene intracellularly, and selecting a cDNA clone introduced into the cell. The partial sequence of the expression regulate protein is preferably a combination of a DNA binding domain and an active domain of a transcription factor. When a yeast is used as a host cell, for example, a DNA binding domain and an active domain of GAL4 protein derived from the yeast can be used. When the Rab protein region and the conjugate factor region of the expressed fusion proteins interact, the activity of GAL4 is completely recovered and GAL4 binds with an upstream activating sequence (UAS) of the host yeast cell to express the reporter gene. When, for example, histidine synthase is used as a reporter gene, culture of the yeast cell in a histidine free medium results in the formation of colonies of only the clones carrying a cDNA wherein one of the vectors encodes a conjugate factor.

It is also possible to use a LexA protein derived from *Escherichia coli* as a DNA binding domain, and an acid blob domain B42 of *Escherichia coli* as the active domain.

A plasmid carrying a DNA encoding the conjugate factor is prepared by a conventional method from the colonies thus obtained, and the base sequence of the incorporated cDNA can be determined using a known sequencing technique such as Maxam-Gilbert method, dideoxy termination method and the like.

A DNA encoding a first conjugate factor capable of specific interaction with the first Rab protein of the present invention is preferably a DNA encoding the amino acid sequence depicted in SEQ ID NO:7, an amino acid sequence which is said amino acid sequence wherein one to several amino acids are deleted, substituted, inserted, added or modified, or a fragment of said amino acid sequence (provided that a protein consisting of the mutated amino acid sequence or the fragment has a physiological activity capable of regulating degranulation of mast cells on its own or by interaction with the Rab protein). More preferably, the DNA encoding a first conjugate factor capable of specific interaction with the first Rab protein of the present invention is a DNA having a base sequence consisting of base Nos. 18–104 of the base sequence depicted in SEQ ID NO:8, a DNA comprising a base sequence which is said base sequence wherein one to several bases are deleted, substituted, inserted or added, or a fragment of said base sequence (provided that a protein encoded by the mutated base sequence or the fragment has a physiological activity capable of regulating degranulation of mast cells on its own or by interaction with the Rab protein).

A DNA encoding a second conjugate factor capable of specific interaction with the first Rab protein of the present invention is preferably a DNA encoding the amino acid sequence depicted in SEQ ID NO:9, an amino acid sequence which is said amino acid sequence wherein one to several amino acids are deleted, substituted, inserted, added or modified, or a fragment of said amino acid sequence (provided that a protein consisting of the mutated amino acid sequence or the fragment has a physiological activity capable of regulating degranulation of mast cells on its own or by interaction with the Rab protein). More preferably, the DNA encoding a second conjugate factor capable of specific interaction with the first Rab protein of the present invention is a DNA having a base sequence consisting of base Nos. 18–68 of the base sequence depicted in SEQ ID NO:10, a DNA comprising a base sequence which is said base sequence wherein one to several bases are deleted, substituted, inserted or added, or a fragment of said base sequence (provided that a protein encoded by the mutated base sequence or the fragment has a physiological activity capable of regulating degranulation of mast cells on its own or by interaction with the Rab protein).

A DNA encoding a third conjugate factor capable of specific interaction with the first Rab protein of the present invention is preferably a DNA encoding the amino acid sequence depicted in SEQ ID NO:11, an amino acid sequence which is said amino acid sequence wherein one to several amino acids are deleted, substituted, inserted, added or modified, or a fragment of said amino acid sequence (provided that a protein consisting of the mutated amino acid sequence or the fragment has a physiological activity capable of regulating degranulation of mast cells on its own or by interaction with the Rab protein). More preferably, the DNA encoding a third conjugate factor capable of specific interaction with the first Rab protein of the present invention is a DNA having a base sequence consisting of base Nos. 18-1334 of the base sequence depicted in SEQ ID NO:12, a DNA comprising a base sequence which is said base sequence wherein one to several bases are deleted, substituted, inserted or added, or a fragment of said base sequence (provided that a protein encoded by the mutated base sequence or the fragment has a physiological activity capable of regulating degranulation of mast cells on its own or by interaction with the Rab protein).

A DNA encoding a conjugate factor capable of specific interaction with the second Rab protein of the present invention is preferably a DNA encoding the amino acid sequence depicted in SEQ ID NO:13, an amino acid sequence which is said amino acid sequence wherein one to several amino acids are deleted, substituted, inserted, added or modified, or a fragment of said amino acid sequence (provided that a protein consisting of the mutated amino acid sequence or the fragment has a physiological activity capable of regulating degranulation of mast cells on its own or by interaction with the Rab protein). More preferably, the DNA encoding a conjugate factor capable of specific interaction with the second Rab protein of the present invention is a DNA having the base sequence depicted in SEQ ID NO:14, a DNA comprising a base sequence which is said base sequence wherein one to several bases are deleted, substituted, inserted or added, or a fragment of the DNA having said base sequence (provided that a protein encoded by the mutated base sequence or the fragment has a physiological activity capable of regulating degranulation of mast cells on its own or by interaction with the Rab protein).

The DNA encoding the first to third conjugate factors capable of specific interaction with the first Rab protein of the present invention can be also chemically synthesized entirely based on the base sequence depicted in SEQ ID NO:8, 10 or 12, according to, for example, the method of Y. A. Ovchinnikov et al. (Gene, vol. 31, pp. 65–78 (1984)), respectively. The DNA encoding the conjugate factor capable of specific interaction with the second Rab protein of the present invention can be chemically synthesized entirely likewise based on the base sequence depicted in SEQ ID NO:14.

The present invention also provides a recombinant vector containing a DNA encoding Rab protein or a conjugate factor capable of a specific interaction therewith in the present invention. The recombinant vector of the present invention is not particularly limited as long as it can afford replicatable retention or autonomous growth in various host cells such as prokaryocyte or eukaryocyte, and encompasses plasmid vectors, virus vectors and the like. This recombinant vector can be conveniently prepared by connecting a known cloning vector or expression vector available in this technique field with the above-mentioned each DNA using a suitable restriction enzyme and ligase, or where necessary, a linker or adaptor DNA. Such vector is exemplified by pBR322, pBR325, pUC18, pUC19 and the like as a plasmid derived from *Escherichia coli*, pSH19, pSH15 and the like as a plasmid derived from yeast, and pUB110, pTP5, pC194 and the like as a plasmid derived from *Bacillus subtilis*. As a virus, there are mentioned bacteriophage (e.g., λ phage etc.), animal and insect viruses such as papovavirus (e.g., SV40, bovine papilloma virus (BPV) etc.), retrovirus (e.g., Moloney mouse leukemia virus (MoMuLV) etc.), adenovirus (AdV), adeno-associated virus (AAV), vaccinia virus, baculovirus and the like.

Particularly, the present invention provides an expression vector containing a DNA encoding a Rab protein or a conjugate factor thereof under regulate of a promoter functional in an objective host cell. The vector to be used is not particularly limited as long as it includes a promoter region that functions in various host cells such as prokaryocyte and eucaryocyte and can regulate transcription of a gene located downstream thereof (e.g., trp promoter, lac promoter, lecA promoter etc. when the host is *Escherichia coli*, SPO1 promoter, SPO2 promoter, penP promoter etc. when the host is *Bacillus subtilis*, PHO5 promoter, PGK promoter, GAP promoter, ADH promoter etc. when the host is a yeast, virus promoters such as SV40-derived early promoter, MoMuLV-derived long terminal repeat, adenovirus-derived early promoter etc. when the host is a mammalian cell) and a transcription termination signal or a terminator region of this gene, and this promoter region and said terminator region are ligated via a sequence containing at least one restriction enzyme recognition site, preferably a unique restriction site that cleaves the vector at said site alone. However, it is preferable that it further contain a selection marker gene (a gene imparting resistance to a pharmaceutical agent such as tetracycline, ampicillin, kanamycin and the like or a gene that complements nutrition requirement mutation) for selection of the transformant. When a DNA encoding the Rab protein or conjugate factor to be inserted does not contain an initiation codon and a termination codon, a vector containing an initiation codon (ATG) and a termination codon (TAG, TGA, TAA) at downstream of the promoter region and at upstream of the terminator region, respectively, is preferably used.

When bacteria is used as a host cell, the expression vector generally needs to contain, in addition to the above-mentioned promoter region and terminator region, a replicatable unit capable of autonomous replication in the host cell. A promoter region encompasses an operator and a Shine-Dalgarno (SD) sequence in the vicinity of the promoter.

When a yeast, animal cell or insect cell is used as a host, the expression vector preferably further contains an enhancer sequence, a non-translation region on the 5' side and the 3' side of a Rab protein or a conjugate factor thereof, a polyadenylation site and the like.

The present invention also provides a transformant obtained by transforming a host cell with the above-mentioned expression vector. The host cell to be used in the present invention is free of any particular limitation as long as it is compatible with the aforementioned expression vector and can be transformed, and various cells are used, including natural cells or mutant cells established artificially or recombinant cells and the like, which are generally used in the technical field of the present invention [e.g., bacteria (*Escherichia coli, Bacillus subtilis, Lactobacillus* etc.), yeast (the genera *Saccharomyces, Pichia, Kluyveromyces* etc.), animal cells (e.g., mammalian cells, particularly cells of human, monkey, mouse, rat, hamster and the like, which are specifically mouse-derived cells such as COP, L, C127, Sp2/0, NS-1, NIH3 T3 and the like, rat-derived cells, hamster-derived cells such as BHK, CHO and the like, simian-derived cells such as COS1, COS3, COS7, CV1, Vero and the like, and human-derived cells such as HeLa, diploid fibroblast strain-derived cell, myeloma cell, Namalwa and the like), insect cells and the like].

Introduction of an expression vector into a host cell can be conducted according to a conventionally known method. For example, transformation is possible by the method of Cohen et al. (Proc. Natl. Acad. Sci. USA, 69, 2110 (1972)), protoplast method (Mol. Gen. Genet., 168, 111 (1979)), competent method (J. Mol. Biol., 56, 209 (1971)) and the like in the case of bacteria, by the method of Hinnen et al. (Proc. Natl. Acad. Sci. USA, 75, 1927 (1978)), lithium method (J. Bacteriol., 153, 163 (1983)) and the like in the case of yeast, by the method of Graham (Virology, 52, 456 (1973)) and the like in the case of animal cells, and by the method of Summers et al. (Mol. Cell. Biol., 3, 2156–2165 (1983)) and the like in the case of insect cells.

The Rab protein and a conjugate factor thereof in the present invention can be produced by culturing a transformant containing an expression vector prepared as mentioned above in a medium and recovering the protein from the obtained culture.

The medium to be used preferably contains a carbon source, an inorganic nitrogen source or an organic nitrogen source necessary for the growth of the host cell (transformant). The carbon source is exemplified by glucose, dextran, soluble starch, sucrose and the like, and the inorganic nitrogen source and the organic nitrogen source are exemplified by ammonium salts, nitrates, amino acid, corn steep liquor, peptone, casein, meat extract, soybean cake, potato extract and the like. Where desired, other nutrients [for example, inorganic salts (e.g., calcium chloride, sodium dihydrogen phosphate, magnesium chloride), vitamins, antibiotics (e.g., tetracycline, neomycin, ampicillin, kanamycin etc.) and the like] may be added.

Culture is done according to a method known in this field. Specific examples of the medium and culture conditions employed depending on the host cell are shown in the following, but the culture conditions in the present invention are not at all limited by them.

When the host is bacteria, Actinomycetes, yeast, filamentous bacterium and the like, for example, a liquid medium containing the above-mentioned nutrient sources is suitable. Preferably, the medium has a pH of 5–8. When the host is *Escherichia coli*, preferable medium includes LB medium, M9 medium (Miller. J., Exp. Mol. Genet., p. 431, Cold Spring Harbor Laboratory, New York (1972)) and the like. The culture includes aeration and stirring as necessary and is conducted generally at 14–43° C. for about 3–24 hr. When the host is *Bacillus subtilis*, the culture includes aeration and stirring as necessary and is conducted generally at 30–40° C. for about 16–96 hr. When the host is a yeast, the medium is exemplified by Burkholder minimum medium (Bostian. K. L. et al, Proc. Natl. Acad. Sci. USA, 77, 4505 (1980)) and the pH is preferably 5–8. The culture is conducted generally at about 20–35° C. for about 14–144 hr, with aeration and stirring as necessary.

When the host is an animal cell, the medium may be, for example, minimum essential medium (MEM) (Science, 122, 501 (1952)), Dulbecco's modified minimum essential medium (DMEM) (Virology, 8, 396 (1959)), RPMI1640 medium (J. Am. Med. Assoc., 199, 519 (1967)), 199 medium (Proc. Soc. Exp. Biol. Med., 73, 1 (1950)) and the like, supplemented with about 5–20% fetal bovine serum. The pH of the medium is preferably about 6–8, and the culture is conducted generally at about 30–40° C. for about 15–72 hr, with aeration and stirring as necessary.

When the host is an insect cell, the medium may be, for example, Grace's medium (Proc. Natl. Acad. Sci. USA, 82, 8404 (1985)) and the like, supplemented with fetal bovine serum. The pH of the medium is preferably about 5–8, and the culture is conducted generally at about 20–40° C. for about 15–100 hr, with aeration and stirring as necessary.

The Rab protein and a conjugate factor thereof are purified by centrifugation or filtration of the culture to collect cells, suspending the cells in a suitable buffer, rupturing (lysis) the cell and organelle membranes by, for example, ultrasonication, lysozyme treatment, freeze and thawing, osmotic shock and/or a treatment with surfactant such as Triton-X100 etc. and the like, removing the debris by centrifugal separation, filtration and the like to give a soluble fraction, treating the soluble fraction by a method similar to that mentioned above, thereby performing isolation and purification.

The method for quickly and conveniently obtaining a recombinant protein is preferably exemplified by a method comprising adding a DNA sequence encoding an amino acid sequence (e.g., sequence consisting of basic amino acids, such as histidine, arginine, lysine and the like, preferably a sequence consisting of histidine) capable of adsorbing to a metal ion chelate to a part containing a code sequence of the protein (preferably C-terminal) by genetic engineering to allow expression in the host cell, and separating and recovering the desired recombinant protein from the culture of the cell by affinity for a carrier on which the metal ion chelate has been immobilized. For example, the DNA sequence encoding an amino acid sequence capable of adsorbing to a metal ion chelate can be introduced into a sequence coding the desired protein by, during the process of cloning the DNA encoding the protein, PCR amplification using a hybrid primer of a base sequence encoding C-terminal amino acid sequence of said protein ligated with the DNA sequence, or insertion of the DNA encoding the protein into an expression vector containing the DNA sequence before the termination codon after aligning the reading frame (i.e., in frame). The metal ion chelate adsorbent to be used for the purification can be prepared by bringing a solution containing a transition metal (e.g., a divalent ion of cobalt, copper, nickel or iron, or a trivalent ion of iron or aluminum, and the like, preferably a divalent ion of cobalt or nickel) into contact with a matrix, to which a ligand such as iminodiacetic acid (IDA) group, nitrilotriacetic acid (NTA) group, tris(carboxymethyl)ethylenediamine (TED) group and the like has been attached, to allow binding with the ligand. The matrix portion of the chelate adsorbent is not particularly limited as long as it is a typical insoluble carrier.

Alternatively, a recombinant protein can be obtained quickly and conveniently by constructing an expression vector prepared such that a DNA encoding a Rab protein or a conjugate factor thereof is expressed as a fusion protein with a known protein that can be purified utilizing a specific affinity for a known affinity column, culturing a transformant, into which the vector has been introduced, to produce the fusion protein, and subjecting the fusion protein to chromatography using a suitable affinity column. Preferably, a method comprising expressing the protein of the present invention as a fusion protein with a glutathione-S-transferase (GST), and subjecting the resulting protein to affinity chromatography using a glutathione-matrix adsorbent (e.g., glutathione—sepharose column) is exemplified. As a vector capable of easily affording such GST fusion protein, commercially available pGEX4T1 (manufactured by Pharmacia) and the like can be used.

The present invention also provides an antibody having specific affinity for the Rab protein and a conjugate factor thereof in the present invention. The antibody may be a polyclonal antibody or a monoclonal antibody and can be prepared by a known immunological method.

For example, a polyclonal antibody can be obtained by subcutaneously or intraperitoneally administering a Rab protein, a conjugate factor thereof, or a fragment thereof (where necessary, it can be also formed into a complex crosslinked with a carrier protein such as bovine serum albumin, KLH (Keyhole Limpet Hemocyanin) and the like) as an antigen, together with a commercially available adjuvant (e.g., complete or incomplete Freund's adjuvant), to an animal about 2–4 times every 2–3 weeks (antibody titer of serum from partially drawn blood is to be measured by a known antigen-antibody reaction and an increase thereof is to be confirmed), collecting the whole blood about 3–10 days after final immunization and purifying an antiserum. An animal to give the antigen is, for example, a mammal such as rat, mouse, rabbit, goat, guinea pig, hamster and the like.

A monoclonal antibody can be prepared by the cell fusion method (e.g., Takeshi Watanabe, Principles of cell fusion method and preparation of monoclonal antibody, pp. 2–14, Monoclonal antibody and cancer—Fundamental and Clinic—, Akira Taniuchi, Toshitada Takahashi eds., Science Forum Publishing (1985)). For example, the factor is subcutaneously or intraperitoneally administered 2–4 times to a mouse together with a commercially available adjuvant, and 3 days after final administration, the spleen or lymph node is taken and leukocytes are recovered. Cell fusion of the leukocytes and myeloma cells (e.g., NS-1, P3X63Ag8 etc.) gives a hybridoma that produces a monoclonal antibody against the factor. The cell fusion may be performed by a PEG method (R. D. Lane, J. Immunol. Methods, vol. 81 No. 2, pp. 223–228 (1985)) or a voltage pulse method (U. Karsten et al., Hybridoma, vol. 7 No. 6, pp. 627–633 (1988)). The hybridoma that produces the desired monoclonal antibody can be selected by detecting an antibody that specifically binds with an antigen from a culture supernatant using known EIA or RIA method and the like. The hybridoma that produces a monoclonal antibody can be cultured in vitro or in vivo in ascites of mouse or rat, preferably mouse, and the like, wherein the antibody can be obtained from the hybridoma culture supernatant and ascites of an animal, respectively.

The present invention also provides a method for assaying the Rab protein and a conjugate factor thereof in the present invention in a sample using the antibody obtained as mentioned above, and a reagent for the assay. This assay method may be based on any known principle as long as it utilizes a specific antigen-antibody reaction with the antibody of the present invention. For example, such method includes immobilizing, by a conventional method, the polyclonal antibody or monoclonal antibody obtained as mentioned above on a solid phase, bringing it into contact with a sample to form an antigen-antibody complex, separating a liquid phase, bringing it into contact with a secondary antibody labeled with an enzyme, fluorescence substance, radioactive isotope and the like to form a sandwich complex and measuring the amount of the label on the solid phase, and the like. The reagent of the present invention for measuring the antigen is free of any particular limitation as long as it contains the antibody of the present invention, which is against the assay target antigen.

The Rab protein and a conjugate factor thereof in the present invention have a physiological activity to regulate degranulation of mast cells by interaction. Both factors can suppressively regulate degranulation on their own when exogenously supplied to mast cells. Since the Rab protein is a GTP binding protein, it shows a GTP/GDP binding activity and is considered to exhibit its physiological activity in link with the conversion reaction due to the GTPase activity of its own. Therefore, (1) a substance capable of inhibiting expression of the Rab protein and/or its conjugate factor in the present invention in mast cells, (2) a substance capable of inhibiting GTP binding activity of the Rab protein, (3) a substance capable of inhibiting GTPase activity of GTP binding Rab protein and (4) a substance capable of inhibiting specific interaction (i.e., binding) between Rab protein and its conjugate factor are capable of ultimately inhibiting degranulation of mast cells, and useful as a therapeutic drug of various diseases in which the degranulation is involved, particularly allergic rhinitis, allergic conjunctivitis, allergic asthma, atopic dermatitis, immediate food-allergy and the like.

The inhibitory substance of the type of the above-mentioned (1) is exemplified by, but not limited to, a nucleotide having a base sequence complementary to a part or the entirety of mRNA encoding the Rab protein and a conjugate factor thereof in the present invention, i.e., anti-sense nucleotide, or an expression vector genetically engineered to express such anti-sense RNA.

The inhibitory substance of the type of the above-mentioned (2) is exemplified by, but not limited to, an exogenously supplied Rab protein or an antibody having specific affinity for the Rab protein of the present invention and the like. It may be a low molecular weight compound or the like, which is known per se or a novel compound.

The inhibitory substance of the type of the above-mentioned (4) is exemplified by, but not limited to, exogenously supplied Rab protein or a conjugate factor itself, or an antibody having specific affinity for the Rab protein or a conjugate factor of the present invention and the like. It may be a low molecular weight compound or the like, which is known per se or a novel compound.

The present invention also provides a screening method of a substance capable of inhibiting interaction between the Rab protein and a conjugate factor thereof in the present invention, i.e., the substance of the type of the above-mentioned (4) that can inhibit degranulation of mast cells.

This screening method includes use of a transformant prepared using the two-hybrid method in one preferable embodiment of the cloning of a cDNA encoding the conjugate factor of the present invention. That is, this method includes culturing, in the presence or absence of a test substance, a transformant obtained by introducing, into a host cell, an expression vector comprising a DNA encoding the Rab protein of the present invention in a form permitting expression as a fusion protein with a partial sequence of a protein that regulates expression of a reporter gene in the host cell, and an expression vector comprising a DNA encoding the corresponding conjugate factor of the present invention in a form permitting expression as a fusion protein with a different partial sequence of said protein (provided that said two partial sequences restore a function to regulate expression of the reporter gene only when the obtained two fusion proteins interact), and comparing the intracellular expression of the reporter gene. The reporter gene, respective partial sequences of said protein that regulates expression, host cell and the like used are the same as those mentioned above. When the test substance has an activity to inhibit the interaction between the Rab protein and a conjugate factor thereof, the expression of the reporter gene is significantly inhibited in the presence of a test substance as compared to the case when the test substance is absent. For example, when a histidine synthase is used as a reporter gene, the substance that inhibits interaction between the Rab protein and its conjugate factor significantly inhibits growth of the transformant in a medium free of histidine.

The present invention also provides a substance capable of inhibiting interaction between the Rab protein and a conjugate factor thereof in the present invention, i.e., a substance capable of inhibiting degranulation of mast cells, which are obtained by the above-mentioned screening method. One example of such inhibitory substance is a compound represented by the formula [I] or [II]

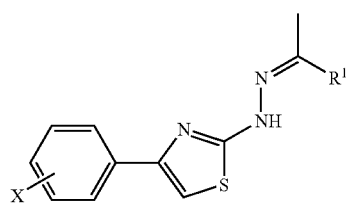

[I]

wherein $R^1$ is a hydrogen atom or a straight chain or branched chain alkyl group having 1 to 4 carbon atoms, and X is a hydrogen atom, a straight chain or branched chain alkyl group having 1 to 4 carbon atoms, a hydroxyl group or a phenyl group

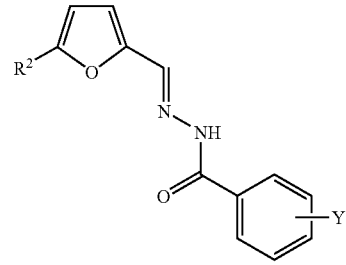

[II]

wherein $R^2$ is a hydrogen atom or a nitro group, and Y is a halogen atom, a straight chain or branched chain alkyl group having 1 to 4 carbon atoms or a hydroxyl group.

Preferably, a substance capable of inhibiting an interaction between the Rab protein and a conjugate factor thereof in the present invention is exemplified by acetone-4-(4-phenyl)phenyl-1,3-thiazol-2-yl-hydrazone, 4-methylpentanone-4-phenyl-1,3-thiazol-2-yl-hydrazone, 2-butanone-4-phenyl-1,3-thiazol-2-yl-hydrazone, 5-nitro-2-furaldehyde-2-brombenzoylhydrazone and the like, but the substance is not limited to them and may be any substance obtained by the above-mentioned screening method.

These compounds can be used as a therapeutic drug of various diseases involving degranulation of mast cells, particularly a therapeutic drug of allergic rhinitis, allergic conjunctivitis, allergic asthma, atopic dermatitis, immediate food allergy and the like. Therefore, the present invention also provides an antiallergic agent containing such compound as an active ingredient.

The antiallergic agent of the present invention can be administered orally in the dosage form of tablet, capsule and the like, or parenterally in the form of injection, inhalant, eye drop or liniment of a solution, suspension and the like with a pharmaceutically acceptable liquid, which contains the inhibitory substance obtained by the above-mentioned screening method. For example, this compound and a pharmaceutically acceptable carrier, flavor, excipient, stabilizer and the like are admixed to afford a preparation for oral administration. The preparation thus obtained can be administered to mammals inclusive of human. While the dose varies depending on the body weight, age and pharmaceutical tolerance of the patients, the kind and progress of the disease, and the like, it is, for example, about 0.01–100 mg, preferably about 0.1–50 mg, daily by oral administration to an adult.

The present invention also provides a screening method of a substance capable of inhibiting the GTP binding activity of the Rab protein of the present invention, i.e., the substance of the type of the above-mentioned (2), that can inhibit degranulation of mast cells.

Specific embodiments of this method are not particularly limited as long as GTP is bound with the Rab protein in the presence or absence of a test substance. For example, a method comprising bringing the Rab protein into contact with a labeled GTP, adding a test substance to a reaction system where GTP binds with the Rab protein, and examining a decrease in the amount of the label bound with the Rab protein.

The present invention also provides a screening method of a substance capable of inhibiting a GTP binding activity of the Rab protein of the present invention and/or an interaction between the Rab protein and a conjugate factor thereof, i.e., the substance of the type of the above-mentioned (2) or (4), that can inhibit degranulation of mast cells.

Specific embodiments of this method are not particularly limited as long as the following steps are conducted in the presence or absence of a test substance:
(1) a step of forming a complex by bringing the Rab protein of the present invention in contact with the corresponding conjugate factor,
(2) a step of binding GTP with the Rab protein (the order of steps (1) and (2) may be reversed or simultaneous),
(3) a step of assaying a complex of the Rab protein bound with GTP and the conjugate factor (provided that any component of the Rab protein, conjugate factor and GTP has been labeled with an enzyme, fluorescence substance, luminescent substance, radioactive isotope and the like).

For example, such method includes adding a test substance to a reaction system, wherein a conjugate factor is immobilized on a solid phase by a conventional method (e.g., specific binding of biotin-avidin etc.). Separately, the corresponding Rab protein is brought into contact with the labeled GTP to form a complex, the complex is brought into contact with a solid phase bound with the conjugate factor to form a complex of labeled GTP—Rab protein—conjugate factor immobilized on solid phase, and examining a decrease in the amount of the label trapped on the solid phase.

The present invention also provides a substance capable of inhibiting GTP binding activity of the Rab protein of the present invention and/or an interaction between the Rab protein and a conjugate factor thereof, which is obtained by the above-mentioned screening method, i.e., a substance capable of inhibiting degranulation of mast cells. Such substance can be used as a therapeutic drug of various diseases in which the degranulation of mast cells is involved, particularly allergic rhinitis, allergic conjunctivitis, allergic asthma, atopic dermatitis, immediate food-allergy and the like. Therefore, the present invention also provides an antiallergic agent containing such compound as an active ingredient.

The antiallergic agent of the present invention containing, as an active ingredient, the inhibitory substance obtained by a screening method using the above-mentioned cell-free system can be formed into a preparation according to a method similar to that of the above-mentioned antiallergic agent obtained by a screening method using a two-hybrid system, and can be administered to mammals inclusive of human by a similar method.

The present invention is described in more detail in the following by referring to Examples. These are mere examples and do not limit the scope of the present invention in any way.

EXAMPLE 1

Cloning of Mouse-Derived Rab Protein cDNA (1) Preparation of Total RNA from Mouse Bone Marrow-Derived Mast Cells.

According to a method reported by T. Nakano et al. (J. Exp. Med., vol. 162, pp. 1025–1043 (1987)), mouse bone marrow-derived mast cells (BMMC) were prepared. Bone marrow cells were taken from the femora of BALB/c mouse, a given number of the cells were suspended in RPMI culture medium containing 10% fetal bovine serum (to be referred to as 10% FBS-RPMI) in a plastic culture dish. A culture supernatant of WEHI-3 cells was added at a concentration of 10–20% and the cells were cultured in the atmosphere containing carbon dioxide at a concentration of 5% at 37° C. The medium was changed to a fresh medium every week and the culture was continued while regulating the cell concentration to a constant level. After 4 weeks of culture, almost homogeneous BMMC was obtained. The total RNA was prepared from this BMMC using a reagent for RNA preparation, ISOGEN (product of NIPPON GENE CO., LTD.) according to the attached protocol.

(2) RT-PCR cDNA was prepared from the total RNA prepared in (1) using a cDNA synthesis reagent kit (manufactured by Pharmacia Biotech). The objective gene was amplified and isolated by PCR using this cDNA as a template DNA and the following two kinds of DNAs I and II as primers.

I: 5'-GGG(G/A)(G/A)(G/C)AGC(G/A)(G/A)CGTGGG(G/C)AA(G/A)(A/T)C-3' (SEQ ID NO:15)

II: 5'-TTC(T/C)TGICC(A/T)GCIGT(G/A)TCCCA-3' (SEQ ID NO:16) (I represents inosine.)

PCR was performed using a reagent attached to a Takara Taq (manufactured by TAKARA) and GeneAmp PCR system 9600 (manufactured by Perkin Elmer) under the following reaction conditions.

denaturation: 94° C., 1 min.

annealing: 50° C., 2 min.

extension: 72° C., 0.5 min.

30 cycle (3) Cloning

The RT-PCR product obtained in (2) was subjected to 2% agarose electrophoresis, and an about 150 bp DNA fragment was recovered using GeneElute AGAROSE SPIN COLUMN (manufactured by Pharmacia Biotech). This DNA fragment was incorporated into a plasmid vector pT7BlueT (manufactured by Novagen) by insertion into a TA cloning site using a DNA ligation kit (manufactured by TAKARA). This recombinant product was introduced into *Escherichia coli* JM109 strain (manufactured by TAKARA) and cultured in an LB agar medium containing ampicillin. Several hundred clones of ampicillin resistant transformed strain were isolated for primary screening.

(4) Determination of Gene Sequence

From among the above-mentioned several hundred clones after primary screening, the plasmid DNAs of about 50 clones were prepared using a QIAGEN plasmid kit (manufactured by QIAGEN). The sequencing reaction using the obtained plasmid DNA as a template, M13 primers M4 and RV (manufactured by TAKARA) as primers and an ABI PRISM Dye Terminator Cycle Sequencing Ready Reaction kit (manufactured by Perkin Elmer) were performed according to the attached manual by GeneAmp PCR system 9600 (manufactured by Perkin Elmer). The reaction product was analyzed by an ABI PRISM 377 DNA sequencer (manufactured by Perkin Elmer). The obtained base sequence was analyzed by a gene information processing soft GENETYX (manufactured by Softwear Development), and as a result, two kinds of 120 bp DNAs (mG#A-DNA and mG#B-DNA) having a novel base sequence were obtained. In addition, known DNAs (8 kinds) encoding Rab protein or low molecular G protein were detected.

(5) Analysis of Expression by Northern Blotting

Using the mG#A-DNA and mG#B-DNA obtained in (4), and a known about 150 bp gene sequence of rab5C as a probe, expression of mRNA in various organs (brain, kidney, spleen, liver, BMMC) of mouse was examined by Northern blotting.

The total RNA derived from each organ was prepared using ISOGEN (manufactured by NIPPON GENE CO., LTD.). From the obtained total RNA, 20 µg was subjected to agarose electrophoresis and transferred to a nylon membrane (manufactured by BioRad) according to a conventional method (reference: Current Protocols in Molecular Biology, vol. 1, 2.5, ed. F. M. Ausubel et al., Wiley Interscience). The mG#A-DNA and mG#B-DNA, and an about 150 bp partial gene sequence of rab5C were $^{32}$P labeled using a BcaBEST Labeling kit (manufactured by TAKARA), and used as a probe. The total RNA derived from each organ, which was immobilized on the nylon membrane and $^{32}$P-labeled probe were hybridized in 250 mM phosphate buffer (pH 7.2) containing 1 mM EDTA, 7% SDS and 0.05 mg/ml salmon sperm DNA at 65° C., washed twice with 40 mM phosphate buffer (pH 7.2) containing 1 mM EDTA and 5% SDS at 65° C., further washed twice with 40 mM phosphate buffer (pH 7.2) containing 1 mM EDTA and 1% SDS at 65° C. and dried. The $^{32}$P labeled probe bond with the RNA on the membrane was autoradiographed with an X ray film for direct radiography (product of Fuji Photo Film Co., Ltd.) for 10 days for detection.

As a result, expression of all the mRNAs of rab5C was detected in every organ, but mRNA containing the sequences of mG#A-DNA and mG#B-DNA was specifically expressed only in mast cells.

(6) Cloning of Full-Length cDNA

The mRNA was prepared from mouse BMMC using an mRNA preparation reagent kit (QuickPrep mRNA Purification kit; manufactured by Pharmacia Biotech). From this mRNA, an EcoRI adaptor-added cDNA was synthesized using a cDNA synthesis reagent kit (TimeSaver cDNA Synthesis kit: manufactured by Pharmacia Biotech). This cDNA was incorporated into an EcoRI site of λ phage vector λgt11 using a DNA ligation kit (manufactured by TAKARA). This cDNA incorporated into the vector was processed using an in vitro packaging kit (GIGAPACK II; manufactured by STRATAGENE) to give phage particles and a λ phage library derived from mast cells was constructed. By plaque hybridization using the above-mentioned mG#A-DNA and mG#B-DNA partial sequences as probes and according to a conventional method (reference: Current Protocols in Molecular biology, vol. 1, 6.1–6.3, ed. F. M. Ausubel et al., Wiley Interscience), phage clones containing full-length cDNAs of the obtained mG#A-DNA and mG#B-DNA were obtained from this library. The obtained clones were incorporated into an EcoRI site of pUC18 and a base sequence was determined. The full length DNAs corresponding to mG#A-DNA and mG#B-DNA were named mG#101-DNA (SEQ ID NO:2) and mG#102-DNA (SEQ ID NO:5), respectively.

EXAMPLE 2

Cloning of Human-Derived Rab Protein cDNA (1) PCR

PCR was performed using a human small intestine-derived cDNA (manufactured by Clontech) as a template and synthetic DNAs (sequences shown in the following) designed based on mG#101 and mG#102 cDNAs as primers.

101p1:5'-GCGAATTCATGCTTCTTG-GAGACTCGGGCGTCGG-3' (SEQ ID NO:17)
101p2:5'-GCGAATTCTCACACAAAGGAGCAG-CAGCTGGAGCG-3' (SEQ ID NO:18)
102p1:5'-GCGAATTCATGCAGACACCTCACAAG-GAGCACCT-3' (SEQ ID NO:19)
102p2:5'-GCGAATTCCTAGGATTTGGCACAGCCA-GAGCAGCT-3' (SEQ ID NO:20)

PCR was performed using a reagent attached to Takara Taq (manufactured by TAKARA) by GeneAmp PCR system 9600 (manufactured by Perkin Elmer) under the following conditions.

denaturation: 94° C., 30 sec.
annealing: 50° C., 15 sec.
extension: 72° C., 40 sec.
35 cycle (2) Subcloning The PCR product obtained in (1) was digested with a restriction enzyme EcoRI and the objective band was purified by agarose electrophoresis. Using a DNA ligation kit (manufactured by TAKARA), it was subcloned to a plasmid vector pUC18. The genetic base sequence of the obtained clone was determined in the same manner as in Example 1 and hG#101 (SEQ ID NO:3) base sequence was obtained for mG#101 and hG#102 (SEQ ID NO:6) base sequence was obtained for mG#102.

EXAMPLE 3

Cloning of Conjugate Factor (Target Molecule) Specific to Mouse-Derived Rab Protein In this Example, experiments were conducted basically following the attached manual of Clontech.

(1) Preparation of Plasmid Library for Two-Hybrid System

By ligating EcoRI adaptor-added cDNA prepared from mouse BMMC in the same manner as in Example 1 to a plasmid vector pACT2 of MATCHMAKER Two-Hybrid System 2 (manufactured by Clontech), a mouse BMMC cDNA library for Two-Hybrid System was prepared.

(2) Preparation of Plasmid for Bait Expression

By incorporating mG#101 or mG#102 full length cDNA, having EcoRI site added to both ends, into EcoRI site of plasmid vector pAS2-1 of MATCHMAKER Two-Hybrid System 2 (manufactured by Clontech), by PCR using the primers used in Example 2, plasmid for bait expression (plasmid incorporating a gene encoding a protein whose bondable protein is desired) was prepared.

(3) Cloning of Conjugate Factor

A plasmid for bait expression and a plasmid library were simultaneously transformed into Saccharomyces cerevisiae CG1945 strain, which is a yeast strain for Two-Hybrid System, to isolate a transformant capable of mG#101 or mG#102-dependent growth in a histidine defective medium. By recovering a plasmid from an isolated transformant, cDNAs of mA#1014 (SEQ ID NO:8), mA#1015 (SEQ ID NO:10), mA#1016 (SEQ ID NO:12) and mA#10283 (SEQ ID NO:14) inserted into pACT2 vector were obtained. The gene sequences of the obtained clones were determined in the same manner as in Example 1.

EXAMPLE 4

Preparation of Recombinant Mouse Rab Protein

In this Example, experiments were conducted basically following the attached manual of Pharmacia Biotech.

(1) Construction of Expression Vector

By incorporating mG#101 or mG#102 cDNA cut out with EcoRI from the bait expression plasmid prepared in Example 3 into an EcoRI site of plasmid vector pGEX4T1 of GST Gene Fusion System (manufactured by Pharmacia Biotech), a plasmid capable of expression of fusion protein with GST was obtained.

(2) Expression by *Escherichia coli*

*Escherichia coli* JM109 strain was transformed with an expression plasmid to give a recombinant *Escherichia coli*. The obtained recombinant *Escherichia coli* was cultured in a 2YT medium (10 g/L yeast extract, 16 g/L tryptone, 5 g/L NaCl) and expression of recombinant protein was induced with 0.1 mM IPTG during the logarithmic growth later phase. Culture was continued for 4 hr after expression induction to intracellularly accumulate the recombinant protein, and recombinant *Escherichia coli* was harvested by centrifugal separation.

(3) Purification of Recombinant Protein

The collected recombinant *Escherichia coli* was suspended in a phosphate buffered saline (PBS) and this suspension was applied to an ultrasonic disintegrator (manufactured by TOMY) to rupture the recombinant *Escherichia coli*. By centrifugal separation, this rupture liquid was separated between soluble supernatant and insoluble sediment, and the supernatant was suspended in glutathione sepharose of GST Gene Fusion System (manufactured by Pharmacia Biotech) and left standing. Glutathione sepharose was recovered from the suspension by centrifugal separation and washed with PBS. The washed glutathione sepharose was suspended in a thrombin solution (recognizes and cleaves specific amino acid sequence introduced into the fused portion of Rab protein and GST) and left standing, whereby the objective Rab protein bound with the glutathione sepharose as a GST fusion protein was removed from the GST part, thereby liberating the protein from the glutathione sepharose. By centrifugal separation, glutathione sepharose and the objective Rab protein solution were separated, and the objective Rab protein solution was applied to a heparin column to remove thrombin, whereby mG#101 protein (SEQ ID NO:1; amino acid Nos. 45, 115, 138, 165 and 167 were Ala, Val, Met, Arg and Pro, respectively) and mG#102 protein (SEQ ID NO:4; amino acid Nos. 113, 185, 192, 200 and 203 were Thr, Leu, Ile, Pro and Val, respectively) were obtained.

EXAMPLE 5

Property Analysis of Recombinant Rab Protein (1) GTP Binding Activity

In this Example, experiments were conducted basically following the method of Kaibuchi et al. (Methods in Enzymology, vol. 257, pp. 67–68 (1995)). That is, mG#101 or mG#102 recombinant protein and GTP [$\gamma^{35}$S] were mixed in the presence or absence of non-labeled GTP and the mixture was stood for 2 hr. This mixture was dot blotted on a nitrocellulose membrane using a dot blotter (manufactured by BioRad) for B/F separation. This membrane was assayed by Beta Counter Matrix 96 (manufactured by Packard) to confirm specific binding of mG#101 or mG#102 recombinant protein to GTP.

(2) Effect on Degranulation

The recombinant protein was added to a BMMC digitonin degranulation system to examine the effect. BMMC was washed twice with a buffer having the following composition to give a suspension at $2\times10^6$ cells/ml and dispensed to a 96-well U-bottom plate by 0.05 ml/well. Then, mG#101 or mG#102 recombinant protein (0.05 ml/well) was added. Furthermore, 4.5 µM digitonin was added by 0.05 ml/well and the plate was stood at room temperature for 5 min. Thereafter 4 mM $CaCl_2$ was added by 0.05 ml/well and the plate was stood at room temperature for 10 min. After standing, the concentration of histamine liberated in the supernatant was determined by a histamine RIA kit (Eiken Chemical Co., Ltd.).

buffer composition:
20 mM HEPES-NaOH (pH 7.0)
133 mM NaCl
5 mM KCl
0.9 mM $NaH_2PO_4$
8 mM glucose
0.1% BSA (deionized)

As a result, both mG#101 and mG#102 recombinant proteins inhibited degranulation in a concentration dependent manner.

EXAMPLE 6

Preparation and Property Analysis of mA#10283 Recombinant Protein (1) Construction of Expression Vector By incorporating mA#10283 cDNA cut out with EcoRI from the pACT2 vector prepared in Example 3 into an EcoRI site of plasmid vector pGEX4T1 of GST Gene Fusion System (manufactured by Pharmacia Biotech), an expression vector of fusion protein of GST and mA#10283 was obtained.

(2) Expression in *Escherichia coli*

*Escherichia coli* JM109 was transformed with the expression vector to give a recombinant *Escherichia coli*. The obtained recombinant *Escherichia coli* was cultured in a 2YT medium and expression of recombinant protein was induced during the logarithmic growth later phase. Culture was continued after expression induction and *Escherichia coli* wherein recombinant protein was intracellularly accumulated, was harvested by centrifugal separation.

(3) Purification of Recombinant Protein

The harvested recombinant *Escherichia coli* was suspended in PBS and this suspension was applied to an ultrasonic disintegrator to rupture the recombinant *Escherichia coli*. By centrifugal separation, this rupture liquid was separated between soluble supernatant and insoluble sediment, and the supernatant was suspended in glutathione sepharose. Glutathione sepharose was recovered from the suspension by centrifugal separation and washed with PBS. The washed glutathione sepharose was suspended in a reduced glutathione solution, thereby eluting the fusion protein of GST and mA#10283 (SEQ ID NO:13), which was bound with the glutathione sepharose. By dialysis of the eluate, glutathione was removed from the objective protein.

(4) Effect of Recombinant Protein on Degranulation

The recombinant protein was added to the digitonin degranulation system (see Example 5) and the effect was examined. As a result, GST fused mA#10283 recombinant protein inhibited degranulation in a concentration dependent manner.

EXAMPLE 7

System (I) for Determining Effect of Test Substance on Interaction between mG#102 and mA#10283

Two expression vectors respectively incorporating mG#102 in pAS2-1 vector and mA#10283 in pACT2 vector were introduced into S. cerevisiae CG1945 strain to give a recombinant yeast #102 strain (see Example 3). As a control, recombinant yeast VT strain into which plasmid for positive control (pVA3-1, pTD1-1) of MATCHMAKER Two-Hybrid System 2 had been introduced was prepared. The culture media of #102 strain and VT strain that reached confluent by shake culture overnight at 30° C. in an SD medium supplemented with histidine were diluted 200-fold with a fresh histidine defective SD medium (containing 1 mM 3-AT) and dispensed to a 96 well plate by 0.09 ml/well. A PBS solution containing a compound whose effect is desired to be examined was added to each well, PBS was added to the well of 100% control, and 1M 3-AT-containing PBS solution was added to the well of 0% control respectively in a volume of 0.01 ml/well and mixed by a plate shaker MicroMixer E-36 (manufactured by TAITEC). Then, after static culture at 30° C. for 18–20 hr, culture media were suspended in a plate shaker, and turbidity (absorbance at 590 nm) was measured with a 96 well plate spectrophotometer Multiskan BICHROMATIC (manufactured by Labsystems) The data of the turbidity measured were evaluated on conversion to % control based on the turbidity data of 100% control and 0% control. When a common effect appears between the #102 strain and the VT strain, it was considered a nonspecific effect on the two-hybrid system rather than an effect on the interaction between mG#102 and mA#10283.

As a result, the concentration of histidine synthase inhibitor (3-amino-1,2,4-triazole: 3-AT) wherein each recombinant yeast strain grows in a histidine defective SD medium in a reporter gene (histidine synthase)-dependent manner was within the range of 1–10 mM and neither recombinant yeast strain could grow with 100 mM 3-AT.

EXAMPLE 8

System (II) for Determining Effect of Test Substance on Interaction between mG#102 and mA#10283

The N-terminal of the recombinant mA#10283 protein prepared in Example 6 was biotinized using a biotin-labeled reagent EZ-Link-Sulfo-NHS-LC-Biotin (manufactured by Pierce) according to the manual attached to the reagent.

Then, recombinant mG#102 prepared in Example 4 and GTP [$\gamma^{35}$S] were mixed at 0.02 mg/ml and 30 nM, respectively. By standing the mixture for 2 hr, the recombinant mG#102 was activated and labeled with radioisotope (RI). This RI-labeled mG#102 protein (0.1 ml), 0.02 mg/ml biotin-labeled mA#10283 protein (0.1 ml), and a buffer solution (0.02 ml) for assay of a compound whose effect is desired to be examined were mixed and stood for 2 hr. The above-mentioned mixture was transferred to a streptavidin-coated flashplate (manufactured by NEN) at 0.1 ml/well and stood for 1 hr. After standing, the mixture was removed from the flashplate, each well was washed once with a washing buffer, and the radioactivity bound was measured by a plate scintillation counter (TopCount: manufactured by Packard). As a 0% control, a well to which biotin labeled GST was added instead of biotin labeled mA#10283 was used, and as a 100% control, a well to which buffer was added instead of the compound solution was used. composition of assay buffer:

20 mM HEPES-NaOH (pH 7.5)

5 mM $MgCl_2$ 1 mM DTT 0.1% BSA composition of washing buffer:

20 mM HEPES-NaOH (pH 7.5)

20 mM $MgCl_2$

EXAMPLE 9

Screening of Compound Inhibiting Interaction between mG#102 and mA#10283

Using the system shown in Example 7, 0.09 ml each of #102 strain yeast or VT strain yeast (control) was placed in each well of a 96 well plate, and a PBS solution containing a particular compound which is unknown as to its effect on the interaction between mG#102 and mA#10283 was added by 0.01 ml, which was followed by culture at 30° C. for 18–20 hr. Then, the culture medium was suspended in a plate shaker and the turbidity (absorbance at 590 nm) was measured with a 96 well plate absorbance meter. The turbidity of the well to which PBS solution without the compound was added was taken as 100% control and the turbidity of the well to which PBS solution containing 3-AT (final concentration 100 mM) instead of the compound was added was taken as 0% control, and the effect of the compound was evaluated by conversion to percentage. As shown in Table 1, acetone-4-(4-phenyl)phenyl-1,3-thiazol-2-yl-hydrazone (formula [III]) and 5-nitro-2-furaldehyde-2-brombenzoylhydrazne (formula [IV]) specifically suppressed #1022 strain in a dose-dependent manner.

TABLE 1

| #102 strain growth suppressive activity of compound | | | |
|---|---|---|---|
| | | Suppression (% control) of growth of yeast strain | |
| Compound | Compound concentration (μg/ml) | #102 strain | VT strain |
| Formula [III] | 0.3 | 99 | 99 |
| | 1 | 57 | 85 |
| | 3 | 4 | 77 |
| | 10 | 1 | 63 |
| Formula [IV] | 1 | 99 | 102 |
| | 3 | 99 | 102 |
| | 10 | 36 | 98 |
| | 30 | −2 | 63 |

TABLE 1-continued

102 strain growth suppressive activity of compound

| Compound | Compound concentration (μg/ml) | Suppression (% control) of growth of yeast strain | |
|---|---|---|---|
| | | #102 strain | VT strain |

[III]

[IV]

EXAMPLE 10

Supressive Action on Mast Cells Degranulation by Compound Obtained by Screening of Compounds Inhibiting Interaction between mG#102 and mA#10283

BMMC prepared by the method shown in Example 1 was suspended in 10% FBS-containing RPMI at a concentration of $3\times10^6$/ml. To this BMMC was added a mouse monoclonal anti-DNP IgE antibody (manufactured by YAMASA) at 3 μg/ml, and the mixture was stood at room temperature for 30 min. Then, BMMC treated with an IgE antibody was washed with buffer A (133 mM NaCl, 5 mM KCl, 0.9 mM $NaH_2PO_4$, 8 mM glucose, 1 mg/ml BSA, 0.01 mM $CaCl_2$, 20 mM HEPES, pH 7.4) and suspended in buffer A containing 1 mM $CaCl_2$ at a concentration of $3\times10^6$/ml. This BMMC suspension (0.1 ml/well) was added in a 96 well multiplate and a solution of the compound to be examined (0.05 ml/well) and a DNP-HSA (manufactured by Sigma) solution (40 ng/ml, 0.05 ml/well) as an antigen were added. After standing at room temperature for 30 min, the mixture was centrifuged at 1000 rpm for 5 min and the supernatant was recovered for the 96 well multiplate by 0.05 ml/well. To this supernatant was added a 4-methylumbelliferyl-2-acetamide-2-deoxy-β-D-glucopyranoside (manufactured by Funakoshi Co., Ltd., substrate of hexosaminidase) solution (1 mM; in 0.2 M citrate buffer (pH 4.5)) at 0.05 ml/well. After standing at 37° C. for 90 min, 1M Tris solution (0.15 ml) was added to stop the reaction, and the amount of fluorescence in each well was measured by fluoroscan (manufactured by Labo Systems). The suppressive effect of the compound on the degranulation of BMMC was calculated based on the amount of fluorescence in the control group free of addition of the compound as 100%. As a control compound, tranilast was used. As shown in Table 2, acetone-4-(4-phenyl)phenyl-1,3-thiazol-2-yl-hydrazone suppressed degranulation of mast cells in a dose-dependent manner.

TABLE 2

Suppressive effect of acetone-4-(4-phenyl)phenyl-1,3-thiazol-2-yl-hydrazone (formula [III]) on degranulation of mast cells

| Concentration (μg/ml) | Suppression (% control) of degranulation of mast cell | |
|---|---|---|
| | Compound of 7 | tranilast |
| 1 | 102 | 96 |
| 3 | 87 | 90 |
| 10 | 39 | 78 |
| 30 | 20 | 52 |
| 100 | 6 | 22 |

INDUSTRIAL APPLICABILITY

The screening system of the present invention using the Rab protein and the specific conjugate factor thereof in the present invention or a transformant carrying a DNA encoding them is useful for determination of a substance capable of suppressing degranulation of mast cells, because it inhibits interaction between the both factors. Such substance can be used as a therapeutic drug of various allergic diseases caused by promoted or accompanying degranulation of mast cells.

Free text of Sequence Listing
SEQ ID NO:1
  Ala or Val.
  Val or Met.
  Met or Leu.
  Arg or His.
  Pro or Ala.
SEQ ID NO:4
  Thr or Ser.
  Leu or Met.
  Ile or Val.
  Pro or Thr.
  Val or Ala.
SEQ ID NO:15
  Oligonucleotide designed to act as primer for amplifying cDNAs encoding mouse Rab proteins.
SEQ ID NO:16
  Oligonucleotide designed to act as primer for amplifying cDNAs encoding mouse Rab proteins.
SEQ ID NO:17
  Oligonucleotide designed to act as primer for amplifying cDNAs encoding human Rab proteins.
SEQ ID NO:18
  Oligonucleotide designed to act as primer for amplifying cDNAs encoding human Rab proteins.
SEQ ID NO:19
  Oligonucleotide designed to act as primer for amplifying cDNAs encoding human Rab proteins.
SEQ ID NO:20
  Oligonucleotide designed to act as primer for amplifying cDNAs encoding human Rab proteins.

This application is based on application No. 2000-118408 filed in Japan, the contents of which are incorporated hereinto by reference.

The references cited herein, including patents and patent applications, are hereby incorporated in their entireties by reference, to the extent that they have been disclosed herein.

What is claimed is:

1. A purified or isolated:
    (a) protein having the amino acid sequence depicted in SEQ ID NO: 1, or
    (b) fragment of the protein of the above-mentioned (a), which fragment regulates degranulation of mast cells on its own or by interaction with one or more conjugate factors selected from the group consisting of proteins having the amino acid sequences of SEQ ID NO: 7, 9, and 11.

2. The protein of claim 1, which is derived from a human.

3. The protein of claim 1, which is derived from a mouse.

4. A method of identifying a substance that inhibits degranulation of mast cells, which comprises
    (1) bringing the protein of claim 1 in contact with GTP both in the presence and absence of a test substance, and
    (2) comparing the binding of GTP to the protein in the presence and absence of the test substance,
    wherein a decrease in the binding of GTP to the protein in the presence of a test substance is indicative that the test substance inhibits degranulation of mast cells.

5. The protein of claim 1, wherein the protein has the amino acid sequence depicted in SEQ ID NO: 1.

6. The protein of claim 1, wherein the protein is a fragment of (a), which fragment regulates degranulation of mast cells on its own or by interaction with one or more conjugate factors selected from the group consisting of proteins having the amino acid sequences of SEQ ID NO: 7, 9, and 11.

7. A method of identifying a substance that inhibits degranulation of mast cells, comprising
    (1) bringing the protein of claim 1 in contact with GTP and one or more conjugate factors selected from the group consisting of proteins having the amino acid sequences of SEQ ID NO: 7, 9, and 11 both in the presence and absence of a test substance to form a complex, and
    (2) assaying the complex of the protein of claim 1, GTP, and one or more conjugate factors,
    wherein a decrease in the amount of complex formed in the presence of the test substance than in the absence of the test substance is indicative that the test substance inhibits degranulation of mast cells.

* * * * *